(12) United States Patent
Sano et al.

(10) Patent No.: US 12,390,118 B2
(45) Date of Patent: Aug. 19, 2025

(54) SENSOR CONTROL CIRCUIT

(71) Applicant: NIPRO CORPORATION, Osaka (JP)

(72) Inventors: Yoshihiko Sano, Osaka (JP); Katsuya Miyagawa, Osaka (JP); Natsumi Shimazaki, Osaka (JP)

(73) Assignee: Nipro Corporation, Osaka (JP)

( * ) Notice: Subject to any disclaimer, the term of this patent is extended or adjusted under 35 U.S.C. 154(b) by 167 days.

(21) Appl. No.: 18/101,639

(22) Filed: Jan. 26, 2023

(65) Prior Publication Data

US 2023/0172469 A1    Jun. 8, 2023

Related U.S. Application Data

(62) Division of application No. 16/083,919, filed as application No. PCT/JP2017/012328 on Mar. 27, 2017, now Pat. No. 11,589,763.

(30) Foreign Application Priority Data

Mar. 29, 2016   (JP) ................................. 2016-066020
Mar. 29, 2016   (JP) ................................. 2016-066022

(51) Int. Cl.
| | | |
|---|---|---|
| A61B 5/026 | (2006.01) | |
| A61B 5/00 | (2006.01) | |
| A61B 5/0205 | (2006.01) | |
| A61B 5/0215 | (2006.01) | |
| G01P 5/10 | (2006.01) | |

(Continued)

(52) U.S. Cl.
CPC .......... *A61B 5/026* (2013.01); *A61B 5/02055* (2013.01); *A61B 5/0215* (2013.01); *A61B 5/6851* (2013.01); *G01P 5/10* (2013.01); *G01R 19/16571* (2013.01); *G01R 19/16576* (2013.01); *G01R 31/52* (2020.01); *A61B 5/6852* (2013.01);

(Continued)

(58) Field of Classification Search
None
See application file for complete search history.

(56) References Cited

U.S. PATENT DOCUMENTS 4,015,142 A  *  3/1977  Nagaoka .................. H01H 9/54
                                                    327/385
5,139,021 A     8/1992  Sekii et al.
(Continued)

FOREIGN PATENT DOCUMENTS

| CN | 202699093 U | 1/2013 |
|---|---|---|
| JP | 55-065006 | 5/1980 |

(Continued)

*Primary Examiner* — Jacqueline Cheng
*Assistant Examiner* — Samuel C Kim
(74) *Attorney, Agent, or Firm* — Jordan and Koda, PLLC; Steven P. Koda, Esq.

(57) ABSTRACT

A control circuit for a sensor provided in a long member which can be inserted into a lumen to measure the flow velocity of a fluid in the lumen and a measurement device. The control circuit includes a drive circuit supplying a drive current to the sensor. A leakage current detection circuit detects a leakage current and performs an output corresponding to the detected leakage current. The leakage current detection circuit outputs a detection signal in response to detection of a leakage current exceeding a threshold value. A stop circuit stopping supply of the drive current to the sensor by the detection signal is further provided.

7 Claims, 17 Drawing Sheets

(51) Int. Cl.
  *G01R 19/165* (2006.01)
  *G01R 31/52* (2020.01)
(52) U.S. Cl.
  CPC . *A61B 2562/0247* (2013.01); *A61B 2562/222* (2013.01); *A61B 2562/227* (2013.01)

(56) References Cited

U.S. PATENT DOCUMENTS

| | | |
|---|---|---|
| 6,142,958 A | 11/2000 | Ola et al. |
| 6,885,210 B1 * | 4/2005 | Suzuki ............... G01R 31/2621 |
| | | 324/762.01 |
| 2006/0129179 A1 | 6/2006 | Weber et al. |
| 2009/0192413 A1 | 7/2009 | Sela |
| 2014/0180141 A1 | 6/2014 | Millett |
| 2014/0249386 A1 | 9/2014 | Caron et al. |
| 2015/0105654 A1 | 4/2015 | Meyer |
| 2015/0141854 A1 | 5/2015 | Eberle |
| 2016/0262698 A1 | 9/2016 | Mahlin |

FOREIGN PATENT DOCUMENTS

| | | |
|---|---|---|
| JP | 63-216534 A | 9/1988 |
| JP | 2001-504249 A | 3/2001 |
| JP | 2007-296354 A | 11/2007 |
| JP | 2008-522717 A | 7/2008 |
| JP | 2012-183239 A | 9/2012 |
| JP | 2015-501184 A | 1/2015 |
| WO | 97/27802 | 8/1997 |
| WO | 2014/100458 A1 | 6/2014 |
| WO | 2016/009317 A1 | 1/2015 |
| WO | 2015/059578 A2 | 4/2015 |

* cited by examiner

SENSOR CONTROL CIRCUIT

BACKGROUND OF THE INVENTION

The present invention relates to a blood measurement device measuring the physical quantities relating to blood in a blood vessel.

Moreover, the present invention relates to a control circuit for a sensor provided in a long member which can be inserted into a lumen to measure the flow velocity of a fluid in the lumen and a measurement device.

BACKGROUND ART

As one of the indices for determining the course of treatment of a stenotic lesion in a coronary artery, the coronary flow reserve (CFR) is mentioned. The CFR is an index indicating the capability to increase the coronary blood flow rate corresponding to an increase in the myocardial oxygen consumption and is determined based on a ratio of the coronary blood flow rete at the maximum congestion to the coronary blood flow rate at rest. A reduction in the CFR is considered to be the onset mechanism of the myocardial ischemia in view of the coronary circulation. Moreover, when the diameter of the coronary artery does not vary, the CFR is determined as a ratio of the maximum coronary artery blood flow velocity to the coronary artery blood flow velocity at rest because the coronary artery blood flow rate and the coronary artery blood flow velocity are linearly correlated with each other.

The CFR is about 3.0 to 4.0 in a healthy sample but is less than 2.0 in significant stenosis with a diameter stenosis rate (% DS) of 75% or more. Moreover, it has been reported that the CFR reduces also in a minimum coronary artery disease even when the coronary artery is free from significant stenosis. Thus, the CFR is not merely used for the evaluation of the coronary artery diameter stenosis rate but used as a synthetic index of the coronary circulation including the coronary microcirculation.

Patent Document 1 discloses a guide wire provided with a pressure sensor having a temperature sensing member in a tip portion. The pressure sensor is provided in a stainless steel outer tube having an opening portion. The temperature sensing member in the pressure sensor is exposed from the stainless steel outer tube through the opening portion. The temperature sensing member outputs signals corresponding to temperature changes accompanying mass flow rate changes of the blood flow contacting the temperature sensing member through the opening portion. Patent Document 1 describes that the CFR can be calculated only based on output signals of the temperature sensing member.

Patent Document 2 discloses a guide wire assembly having sensors, such as a pressure sensor and a flow rate sensor. The guide wire assembly has a tubular shaft, and a sensor element is provided in an end portion on the distal side of the shaft. A core wire is inserted into and passed through the inside of the shaft. A tip portion of the core wire is inserted into the sensor element. The sensors are mounted in the core wire portion positioned in the sensor element. To the sensor, a cable for, for example, transmitting and receiving signals between the sensor and external devices is connected. The cable is inserted into and passed through the inside of the shaft along the core wire.

When measuring the blood pressure and the like in a blood vessel by the sensor, the guide wire assembly is inserted into the blood vessel with the sensor element as the head. The sensor element is caused to advance in the blood vessel by propulsive force applied to an end portion on the proximal side of the shaft. When the rotational force around the axis line is applied to the end portion on the proximal side in the shaft, the rotational force is transmitted to the sensor element through the shaft. Thus, the sensor element is turned around the axis line.

CITATION LIST

Patent Literature

Patent Document 1: Japanese Unexamined Patent Application Publication (Translation of PCT Application) No. 2001-504249
Patent Document 2: Japanese Unexamined Patent Application Publication (Translation of PCT Application) No. 2007-296354

SUMMARY OF THE INVENTION

The guide wire having the sensors described above has been demanded to be reduced in the size and the diameter so as to be able to be inserted into a small-diameter coronary artery. The guide wire assembly disclosed in Patent Document 2 requires space which the cable is inserted into and passed through together with the core wire in the shaft. However, it is limited to increase the outer diameter of the shaft because the outer diameter of the shaft is set so as to be able to be inserted into a blood vessel. Therefore, when the space which the cable is inserted into and passed through together with the core wire is secured in the shaft having a predetermined outer diameter, the thickness (thickness) of a peripheral surface portion in the shaft needs to be reduced.

When the thickness of the shaft decreases, the bending rigidity of the shaft decreases. When the shaft with low bending rigidity advances the inside of a blood vessel, the shaft is easily curved by the resistance, such as frictional force, with the blood vessel. Thus, there is a possibility that propulsion properties of the sensor element in the blood vessel may be impaired. When the thickness of the shaft is small, the rotational force given to the end portion on the proximal side of the shaft is easily displaced into a state where the peripheral surface portion of the shaft is twisted. Therefore, there is also a possibility that the transmission properties of the rotational force may decrease.

The present invention has been made in view of the above-described circumstances. It is an object of the present invention to provide a blood measurement device having high bending rigidity and having excellent propulsion properties and rotational force transmission properties in a blood vessel.

It is another object of the present invention to provide a safe control circuit for a small sensor measuring the flow velocity of a fluid in a lumen.

(1) A blood measurement device according to the present invention has a tubular shaft having flexibility, a tubular connection portion positioned coaxially with the distal end of the shaft and having an inner diameter larger than the inner diameter of the shaft, a passage communicating the inside and the outside of the connection portion, a tubular tip guide portion having flexibility coaxially connected to the distal end of the connection portion, a core material having flexibility fitted into the connection portion and extending to the distal end in the internal space of the tip guide portion to be connected to the tip guide portion, a measurement element positioned in the internal space of the tip guide portion and measuring the physical quantity of blood, and a signal wire which is extended from the measurement element to be inserted into and passed through the internal space of the shaft through the passage.

In the blood measurement device, the bending rigidity of the tip guide portion is secured by the core material. Moreover, the thickness (thickness) of the peripheral surface portion in the shaft can be reduced, and therefore the bending rigidity of the shaft can be secured by the thickness of the circumferential surface portion of the shaft. Furthermore, the propulsive force and the rotational force to be applied to the shaft can be efficiently transmitted to the tip guide portion by the thickness of the peripheral surface portion of the shaft. Moreover, even in the state where the core material is supported by the connection portion, the signal wire is inserted into and passed through the inside of the connection portion through the passage.

(2) Preferably, the connection portion is integrally formed in the distal end of the shaft.

(3) Preferably, the passage is a slit extending in the axial direction in the connection portion.

(4) Preferably, the passage is a groove extending in the axial direction in the proximal end of the core material.

(5) Preferably, the outer diameter of the connection portion is smaller than the outer diameter of the proximal end of the shaft and the blood measurement device is further provided with a tubular cover member fitted onto the connection portion.

A connection place between the connection portion and the core material is reinforced with a cover member.

(6) Preferably, the proximal end of the core material is positioned between the proximal end and the distal end of the passage.

The above-described configuration makes it difficult for the proximal end of the core material and the signal wire to contact each other.

(7) Preferably, the connection portion has a tubular body portion coaxially connected to the distal end of the shaft and a tubular support portion which is positioned in the distal end in the body portion and into which the core material is fitted.

(8) Preferably, the passage is a slit extending in the axial direction in the support portion.

(9) Preferably, the passage is a groove extending in the axial direction in the proximal end of the core material.

(10) Preferably, the proximal end of the support portion is positioned between the proximal end and the distal end of the body portion.

The above-described configuration makes it difficult for the proximal end and the signal wire of the shaft to contact each other.

(11) Preferably, the inner diameter of the internal space of the shaft is smaller than the outer diameter of the proximal end of the core material.

(12) Preferably, the tip guide portion has a coil body in which a wire is wound in a spiral shape and a tip member positioned in the distal end, in which the core material is connected to the tip member.

According to the configuration, the tip guide portion has preferable bending rigidity.

(13) Preferably, the measurement element measures the pressure of blood.

(14) Preferably, the measurement element measures the flow velocity of blood.

(15) A control circuit of the present invention is a control circuit for a sensor provided in a long member which can be inserted into a lumen to measure the physical quantity of a fluid in the lumen. The control circuit has a drive circuit supplying a drive current to the sensor and a leakage current detection circuit detecting a leakage current and performing an output corresponding to the detected leakage current.

The sensor is inserted into the lumen with the long member. The sensor measures the flow velocity of a fluid flowing through the lumen at an arbitrary position of the lumen. In the measurement, the leakage current detection circuit detects a leakage current. By the detection of the leakage current, the drive of the sensor is stopped, the power supply is turned off, the leakage current is monitored, or a warning is issued, for example.

(16) Preferably, the leakage current detection circuit outputs a detection signal in response to the detection of a leakage current exceeding a threshold value, and a stop circuit stopping the supply of the drive current to the sensor by the detection signal may be further provided in the control circuit of the present invention.

When the leakage current exceeding a threshold value is generated, the current supply to the sensor from the drive circuit is automatically stopped, so that the leakage of a current into a fluid is stopped.

(17) Preferably, the control circuit of the present invention may further have a function switch turning on/off an input of the detection signal from the leakage current detection circuit to the stop circuit.

When it is not appropriate to stop the drive of the sensor, the drive of the sensor can be maintained or resumed by turning off the function switch.

(18) Preferably, the leakage current detection circuit may have at least either one of a first detection circuit detecting a value corresponding to a difference between a predetermined current and a feedback current from the sensor as a leakage current and a second detection circuit detecting a current between the fluid and a ground as a leakage current. The predetermined current is a current corresponding to the drive current of the sensor or a constant current.

The first detection circuit detects the value corresponding to the difference between the predetermined current and the feedback current as a leakage current. More specifically, the first detection circuit detects a current leaking from the sensor. The second detection circuit detects a current between the fluid and the ground as a leakage current. More specifically, the second detection circuit detects not only a leakage current from the sensor but a leakage current from the entire long member to the fluid.

(19) Preferably, the drive circuit has a constant current circuit supplying a constant current to the flow velocity meter and the first detection circuit has a first shunt resistor converting the feedback current from the flow velocity meter into a voltage and a first comparator outputting a first detection signal corresponding to a state in which a voltage corresponding to an output voltage of the first shunt resistor is larger than a voltage corresponding to a drive current to be supplied to the flow velocity meter from the constant current circuit, in which the second detection circuit may have a second shunt resistor connected between a detection electrode disposed so as to be able to contact the fluid and a ground and a second comparator outputting a second detection signal corresponding to a state in which a voltage corresponding to an output voltage of the second shunt resistor is larger than a voltage corresponding to the drive current to be supplied to the sensor from the constant current circuit.

(20) Preferably, the control circuit of the present invention may be further provided with a temperature compensation circuit receiving an input from a detection body provided in the sensor.

The detection body is a thermocouple or a member performing an output corresponding to output changes due to temperature changes in a sensor, for example. The temperature compensation circuit can correct the measured flow velocity. Moreover, even when a leakage current is generated from such a detection body, the leakage current can be promptly detected by the leakage current detection circuit.

(21) The present invention can also be regarded as a measurement device having the control circuit and the sensor.

(22) Preferably, the sensor may be a hot wire flow velocity meter.

The present invention provides a blood measurement device having high bending rigidity and excellent propulsion properties and rotational force transmission properties in a blood vessel.

Moreover, according to the present invention, a small size and small-diameter measurement device measuring the flow velocity of a fluid flowing through a lumen is realized in a state of having a safety function to a leakage current.

DETAILED DESCRIPTION OF THE INVENTION

Hereinafter, preferable embodiments of the present invention are described. It is a matter of course that each embodiment is merely one embodiment of the present invention and each embodiment can be altered in the range where the gist of the present invention is not altered.

First Embodiment

Figure 1:
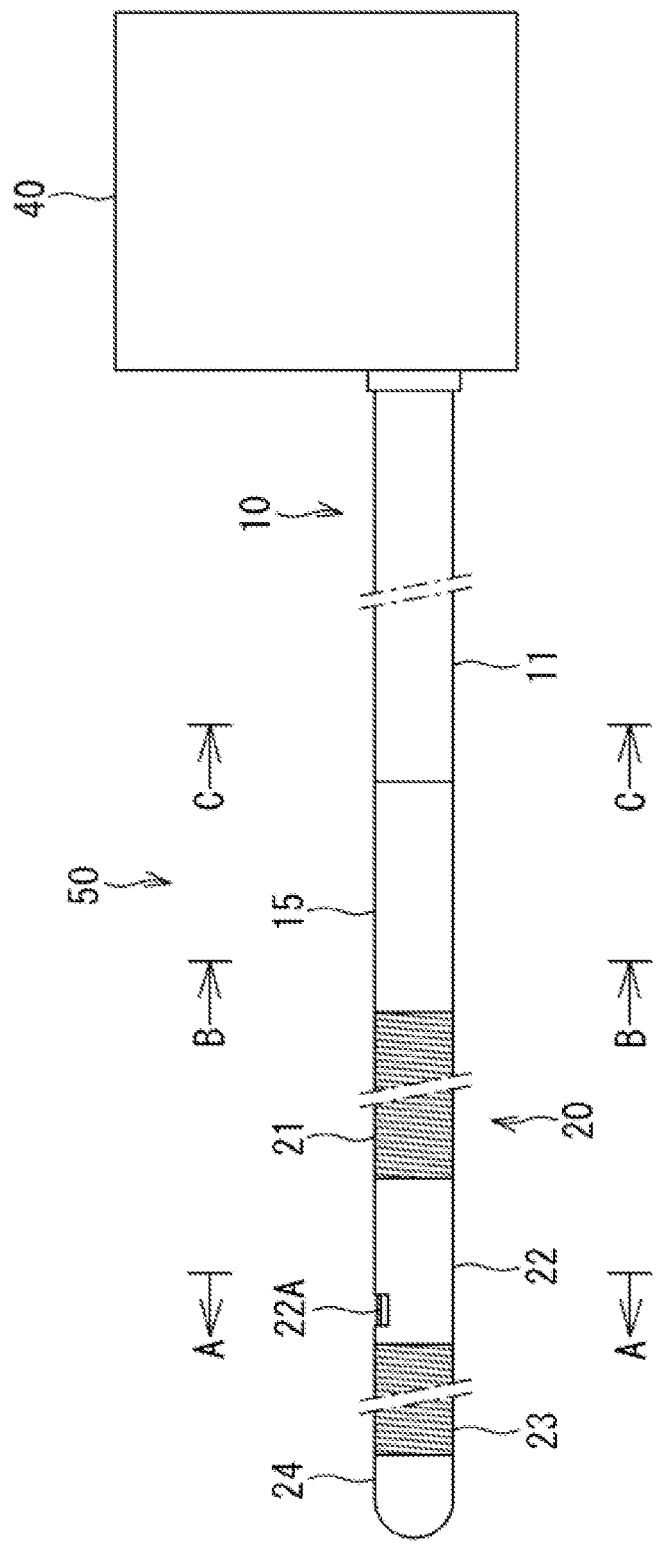
FIG. 1 is a schematic view illustrating the configuration of a blood measurement device 50 according to a first embodiment of the present invention.

Hereinafter, a first embodiment of the present invention is described. A blood measurement device 50 illustrated in FIG. 1 is used for measuring the physical quantities, such as the blood pressure, in a blood vessel of a living body, for example. The blood measurement device 50 has a tubular shaft 10 and a tubular tip guide portion 20 provided in the distal end (equivalent to the tip) of the shaft 10. The tip guide portion 20 is provided with a measurement element 27 (refer to FIG. 2) measuring the pressure of blood in a blood vessel. The proximal end (equivalent to base end) of the shaft 10 is connected to a control device 40 as an external device. The control device 40 controls the electric power to be supplied to the measurement element 27 and processes signals to be transmitted from the measurement element 27, for example.

The shaft 10 is a tubular body having flexibility. The shaft 10 has a length suitable for measuring the blood pressure at a desired position of a blood vessel, which is about 1 to 2 m, for example. The shaft 10 is formed of stainless steel for medical treatment, for example. The outer diameter of the shaft 10 is set corresponding to the thickness of a blood vessel into which the shaft 10 is to be inserted and is several tenths of mm, for example.

Figure 2:
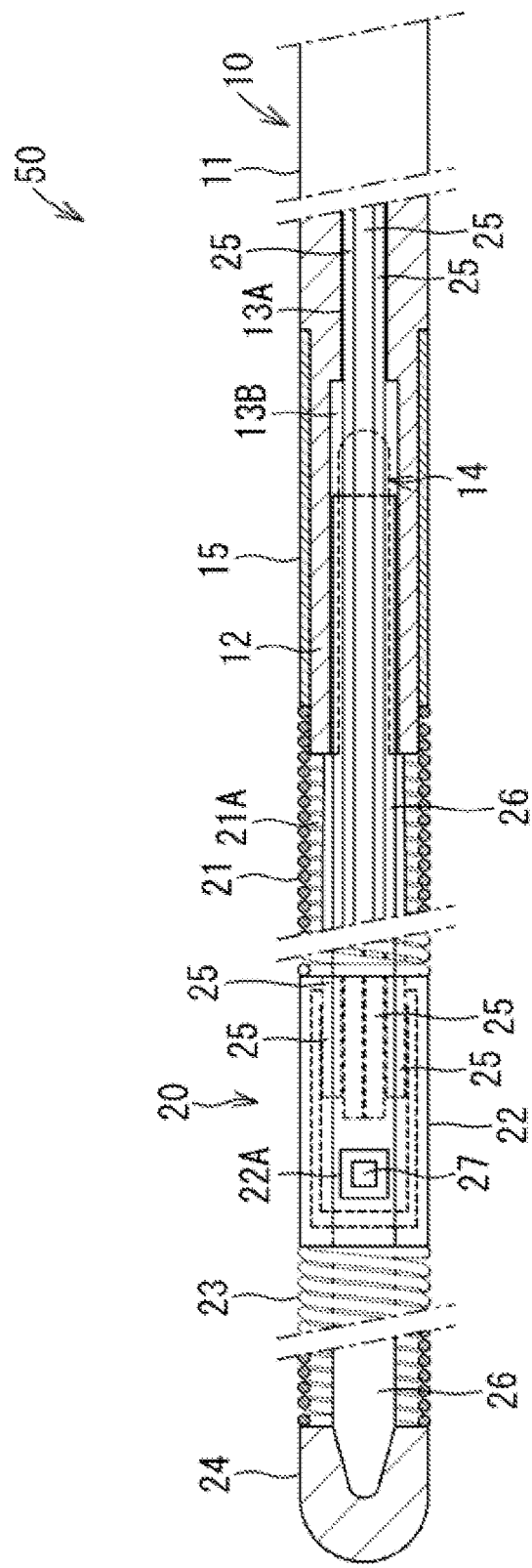
FIG. 2 is a partially-cut plan view of the blood measurement devices 50 illustrated in FIG. 1.

As illustrated in FIG. 2, the shaft 10 has a shaft body portion 11 and a connection portion 12 formed in the distal end of the shaft body portion 11. The shaft body portion 11 is a tubular body having an almost constant outer diameter over the axial direction. An internal space 13A of the shaft body portion 11 also has a constant inner diameter over the axial direction. The connection portion 12 is projected in the axial direction from the distal end of the shaft body portion 11. The connection portion 12 is formed integrally and coaxially with the shaft body portion 11. The "coaxially" means that the axis line of the connection portion 12 and the axis line of the shaft body portion 11 are positioned on the same virtual straight line. Also in the following description, the "coaxially" refers to a state where the axis line of a pair of members each configured into a cylindrical shape are positioned on the same virtual straight line.

The connection portion 12 is a tubular body having an almost constant outer diameter. The outer diameter of the connection portion 12 is smaller than the outer diameter of the shaft body portion 11. The inner diameter of the connection portion 12 is larger than the inner diameter of the shaft body portion 11. An internal space 13A of the shaft body portion 11 and an internal space 13B of the connection portion 12 are caused to communicate with each other. The inner diameter of the internal space 13A of the shaft body portion 11 is set considering the outer diameter of four signal wires 25 to be inserted into and passed through the same in a state of being bundled and the thickness required for the shaft body portion 11.

Figure 3:
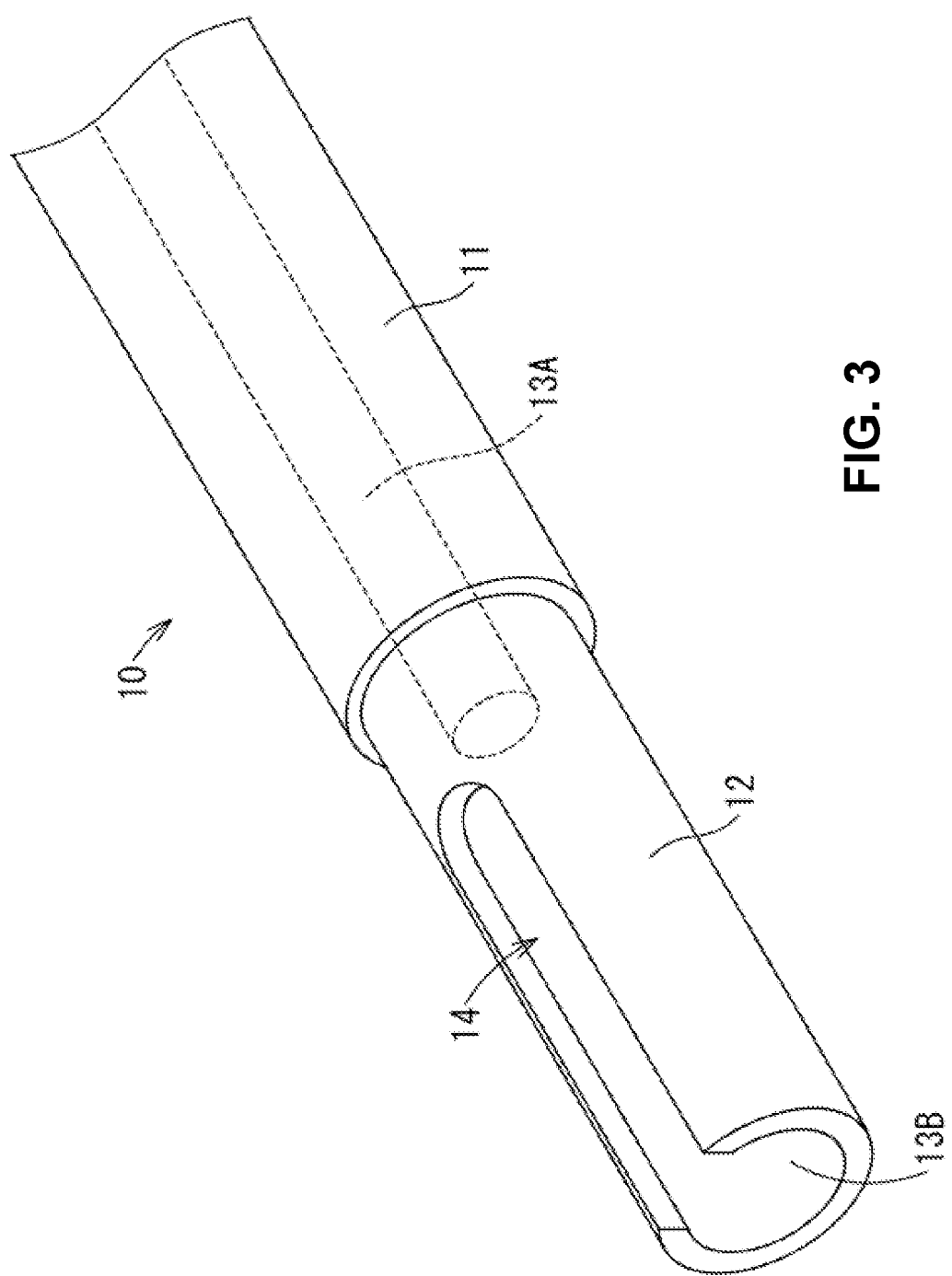
FIG. 3 is a perspective view around a connection portion 12.
Figure 4C:
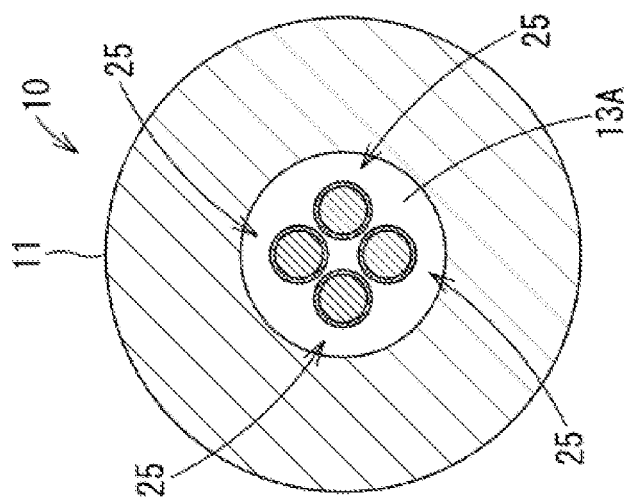
FIG. 4C is a cross-sectional view along the C-C line of FIG. 1.
Figure 4B:
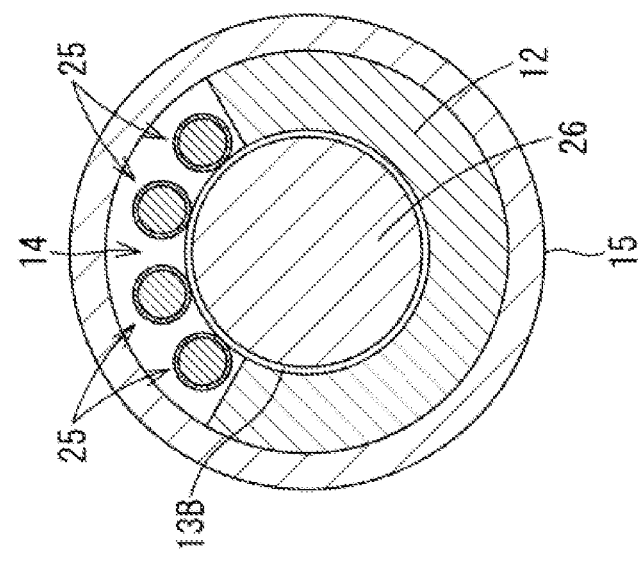
FIG. 4B is a cross-sectional view along the B-B line of FIG. 1.

As illustrated in FIG. 3 and FIG. 4B, the cross section of the connection portion 12 has a C-shape. Due to the fact that an opening portion of the C-shape continues in the axial direction, a slit 14 is formed which extends along the axial direction from the distal end toward the proximal end of the connection portion 12. The slit 14 occupies an about ⅓ range with respect to the outer periphery of the connection portion 12.

A core material 26 is inserted into the internal space 13B of the connection portion 12. The core material 26 is a wire having flexibility and is formed of stainless steel, for example. In the core material 26, the outer diameter is reduced in a tapered shape from the proximal end toward the distal end. The tapered shape of the core material 26 does not need to be formed ranging from the proximal end to the distal end and may be formed in one portion in the range from the proximal end to the distal end.

The core material 26 extends from the internal space 13B toward the distal end of the connection portion 12 to be inserted into and passed through the inside of the tip guide portion 20. The proximal end of the core material 26 is positioned between the proximal end and the distal end of the slit 14 of the connection portion 12. The outer diameter around the proximal end of the core material 26 is equal to the inner diameter of the internal space 13B of the connection portion 12. The vicinity of the proximal end of the core material 26 is fitted into the internal space 13B of the connection portion 12 to be bonded. The outer diameter around the proximal end of the core material 26 is larger than the inner diameter of the internal space 13A of the shaft body portion 11.

As illustrated in FIG. 1 and FIG. 2, the cover member 15 is a tubular body having a constant outer diameter and a constant inner diameter over the axial direction. The cover member 15 is formed of stainless steel or resin, such as polyimide, for example. The outer diameter of the cover member 15 is equal to the outer diameter of the shaft body portion 11 in the shaft 10. The inner diameter of the cover member 15 is equal to the outer diameter of the connection portion 12 in the shaft 10. The dimension along the axial direction of the cover member 15 is shorter than the dimension along the axial direction of the connection portion 12. Therefore, the distal end of the connection portion 12 is projected outward from the cover member 15 in a state where the cover member 15 is fitted onto the connection portion 12 of the shaft 10.

As illustrated in FIG. 2, the tip guide portion 20 has a first coil body 21 connected to the distal end of the connection portion 12, an element holding body 22 connected to the distal end of the first coil body 21, a second coil body 23 connected to the distal end of the element holding body 22, and a tip member 24 provided in the distal end of the second coil body 23. FIG. 2 illustrates constituent components in a longitudinal cross section except the element holding body 22, the distal end of the first coil body 21, and the proximal end of the second coil body 23. Therefore, the element holding body 22 is illustrated in a plan view.

In the first coil body 21, a stainless steel wire having a constant diameter is wound around in a spiral shape having a constant diameter, for example. The proximal end of the first coil body 21 is fitted onto the outside of the distal end of the connection portion 12. The outer diameter of the first coil body 21 is equal to the outer diameter of the cover member 15. The core material 26 and the four signal wires 25 are inserted into and passed through an internal space 21A of the first coil body 21 along the axial direction. Therefore, the inner diameter of the first coil body 21 is sufficiently larger than the outer diameter of the core material 26.

Figure 4A:
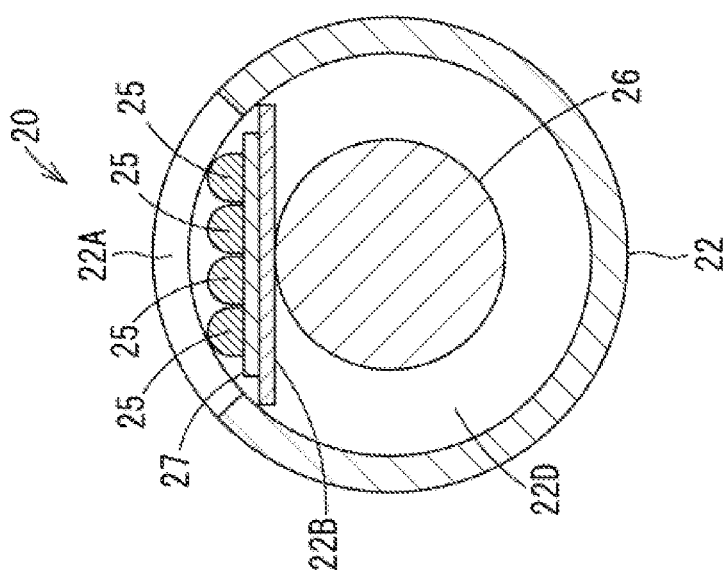
FIG. 4A is a cross-sectional view along the A-A line of FIG. 1.

As illustrated in FIG. 2 and FIGS. 4A-4C, the element holding body 22 holds the measurement element 27. The element holding body 22 has a cylindrical shape and is formed of stainless steel, for example. The element holding body 22 is coaxially connected to the distal end of the first coil body 21. As illustrated in FIG. 4A, the core material 26 is inserted into and passed through an internal space 22D of the element holding body 22 along the axial direction. In a part of the peripheral wall of the element holding body 22, an opening portion 22A is provided. In the internal space 22D of the element holding body 22, a support plate 22B on which the measurement element 27 is to be mounted is provided. The support plate 22B is disposed between the core material 26 inserted into and passed through the internal space 22D and the opening portion 22A of the element holding body 22. The support plate 22B has a flat plate shape and one of the front and rear side surfaces serving as the maximum surface faces the opening portion 22A. The measurement element 27 is a pressure sensor, for example. The measurement element 27 is mounted on one of the front and rear side surfaces of the support plate 22B facing the opening portion 22A.

For the measurement element 27, a configuration known as a pressure sensor is adopted. For example, the measurement element 27 has a diaphragm which is bent by pressure and outputs an electric signal corresponding to the bending amount. To the measurement element 27, the four signal wires 25 are connected, for example. The four signal wires 25 are used for supplying electric power to the diaphragm, transmitting output signals from the diaphragm, and the like. The four signal wires 25 are extended from the measurement element 27 to the proximal side in the internal space 22D of the element holding body 22. In the four signal wires 25, leads are insulation-coated with an external coating material.

As illustrated in FIG. 2, each signal wire 25 is inserted into and passed through the inside of the element holding body 22 to be inserted into and passed through the inside of the first coil body 21 along the axial direction. Moreover, the four signal wires 25 reach the internal space 13B of the connection portion 12 through the slit 14 of the connection portion 12. The four signal wires 25 are inserted into and passed through the internal space 13A of the shaft body portion 11 from the internal space 13B of the connection portion 12 along the axial direction to be electrically connected to the control device 40.

In the second coil body 23, a stainless steel wire having a constant diameter is wound in a spiral shape having a constant diameter, for example. The proximal end of the second coil body 23 is coaxially connected to the distal end of the element holding body 22. The core material 26 is inserted into and passed through the inside of the second coil body 23 along the axial direction.

The tip member 24 is formed of stainless steel in a hemisphere shape, for example. The tip member 24 is attached to the distal end of the second coil body 23. To the tip member 24, the tip of the core material 26 inserted into and passed through the inside of the second coil body 23 is connected.

[Method for Assembling Blood Measurement Device 50]

The blood measurement device 50 is assembled by assembling the tip guide portion 20 and the core material 26 beforehand, fitting the cover member 15 onto the connection portion 12 of the shaft 10, and then connecting them.

Figure 5:
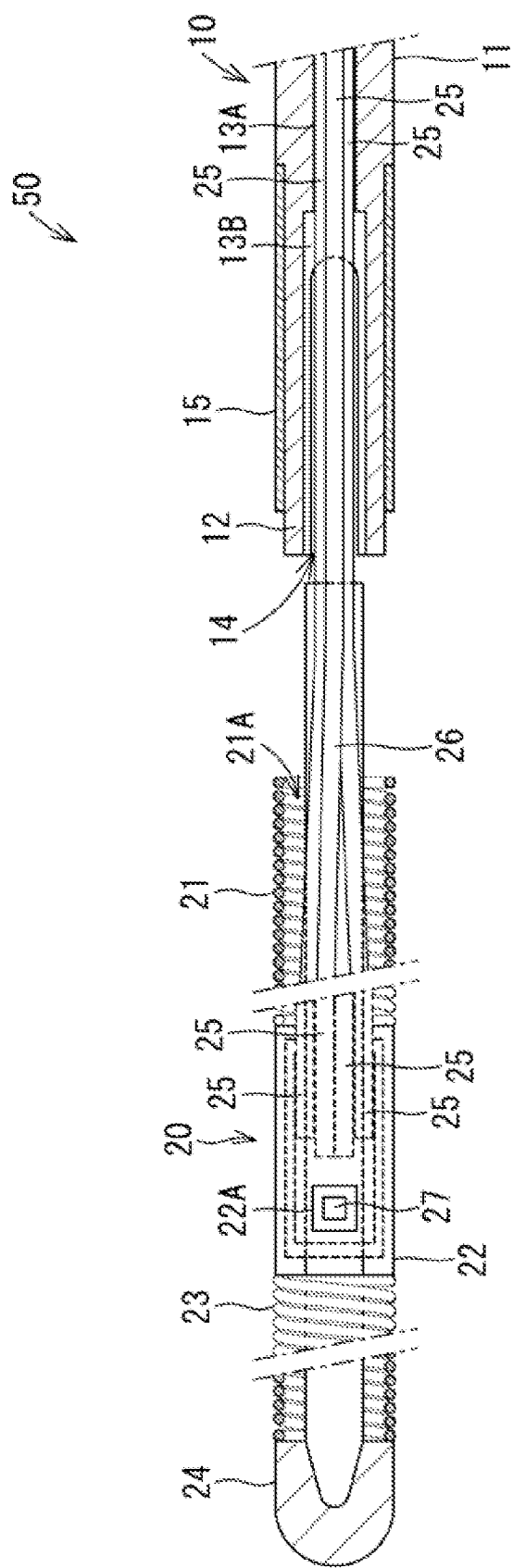
FIG. 5 is an exploded view of a tip guide portion 20, a shaft 10, and a cover member 15.

The tip guide portion 20 is obtained by integrally assembling the first coil body 21, the element holding body 22, the second coil body 23, the tip member 24, and the core material 26 as illustrated in FIG. 5. When the tip guide portion 20 has the other constituent members, the other constituent members are also integrally assembled. In the assembled tip guide portion 20, the core material 26 is extended to the outside from the proximal end of the first coil body 21. The four signal wires 25 are also extended to the outside from the proximal end of the first coil body 21. The cover member 15 is fitted onto the connection portion 12 of the shaft 10.

When the tip guide portion 20, the shaft 10, and the cover member 15 are combined, the four signal wires 25 extending from the tip guide portion 20 are caused to enter the internal space 13B through the slit 14 of the connection portion 12, and further inserted into and passed through the internal space 13A of the shaft body portion 11. Then, the core material 26 extending from the tip guide portion 20 is inserted into the internal space 13B of the connection portion 12 to be fitted thereinto. The proximal end of the core material 26 is positioned between the proximal end and the distal end of the slit 14, so that the signal wires 25 extend to the inside and the outside of the connection portion 12 through the slit 14 which is not closed by the core material 26. The core material 26 and the connection portion 12 are bonded with an adhesive or the like. The proximal end of the first coil body 21 is fitted onto the outside of the distal end of the cover member 15. The first coil body 21, the connection portion 12, and the cover member 15 are bonded with an adhesive. Thus, the blood measurement device 50 is assembled.

[Operational Effects of First Embodiment]

The blood measurement device 50 is used for measuring the changes of the blood pressure at a predetermined position in a coronary artery, for example. In this case, the blood measurement device 50 is inserted into a blood vessel with the tip member 24 as the head. The blood measurement device 50 inserted into the blood vessel is caused to advance in the blood vessel by the application of force (propulsive force) toward the distal end to an end portion on the proximal side of the shaft 10. The tip member 24 inserted into the blood vessel is directed in a predetermined direction by the rotational operation of the end portion on the proximal side of the shaft 10 around the axis line.

The position of the tip member 24 in the blood vessel can be grasped based on the position of the tip member 24 in an X-ray transmission image of the blood vessel.

Due to the fact that the tip member 24 is caused to advance in the blood vessel, the element holding body 22 is positioned at a predetermined portion in the blood vessel. When the end portion on the proximal side of the shaft body portion 11 is rotationally operated around the axis line in such a state, the rotational force given to the shaft body portion 11 is transmitted to the tip guide portion 20 through the connection portion 12. Thus, the tip guide portion 20 is rotated around the axis line.

In this case, only the signal wires 25 may be inserted into and passed through the internal space 13A of the shaft body portion 11, and therefore thickness of the shaft body portion 11 can be increased. Thus, the shaft body portion 11 is difficult to be twisted by the rotational force given to the shaft body portion 11. Thus, the rotation given to the shaft body portion 11 is efficiently transmitted to the tip guide portion 20.

In the blood measurement device 50 of this embodiment, the shaft body portion 11, the connection portion 12, and the tip guide portion 20 are all coaxially configured. Thus, the rotational force transmission properties of the shaft body portion 11, the connection portion 12, and the tip guide portion 20 are entirely further improved. As a result, the tip guide portion 20 is efficiently rotated following the rotational force given to the shaft body portion 11, so that the rotation followability of the tip guide portion 20 is improved.

The opening portion 22A of the element holding body 22 is directed in a predetermined direction by the rotation of the tip guide portion 20. Thus, the detection surface of the measurement element 27 is also directed in the same direction as the direction in which the opening portion 22A is directed. In such a state, the pressure of the blood flowing through the inside of the blood vessel is measured by the measurement element 27. When the blood flows into the element holding body 22 from the opening portion 22A of the element holding body 22, the blood abuts on the detection surface of the measurement element 27. Thus, the measurement element 27 detects the pressure of the blood, and then outputs a predetermined signal to the control device 40 through the signal wires 25. The control device 40 calculates the blood pressure based on the signal transmitted from the measurement element 27.

Since the cover member 15 is fitted onto the connection portion 12 of the shaft 10, the connection portion 12 or the core material 26 are difficult to be broken or the like, even when the connection place between the connection portion 12 and the core material 26 is bent.

Since the proximal end of the core material 26 is positioned between the proximal end and the distal end of the slit 14, space in which the signal wires 25 are movable is provided in the slit 14. Thus, even when the connection place between the connection portion 12 and the core material 26 is bent, the proximal end and the signal wires 25 of the core material 26 become difficult to contact.

Second Embodiment

Hereinafter, a second embodiment of the present invention is described. The connection portion 12 is integrally formed with the shaft body portion 11 in the first embodiment described above. However the connection portion of the present invention may be configured as a member separate from the shaft 10. In the following description, those designated by the same reference numerals as those of the first embodiment refer to the same members.

Figure 6:
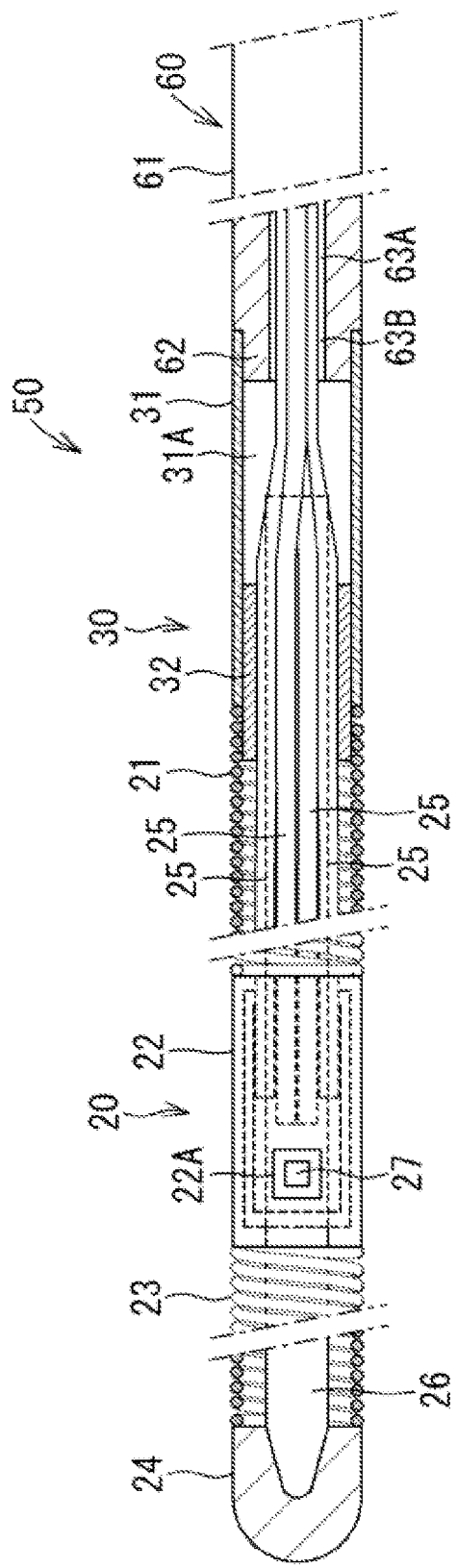
FIG. 6 is a partially-cut plan view of a blood measurement device 50 according to a second embodiment of the present invention.

As illustrated in FIG. 6, a shaft 60 has a shaft body portion 61 and a boss portion 62 provided in the distal end of the shaft body portion 61. The shaft body portion 61 is a tubular body having an almost constant outer diameter over the axial direction. An internal space 63A of the shaft body portion 61 has a constant inner diameter over the axial direction. The boss portion 62 is projected in the axial direction from the distal end of the shaft body portion 61. The boss portion 62 is integrally formed with the shaft body portion 61. Therefore, the internal space 63A of the shaft body portion 61 and an internal space 63B of the boss portion 62 have the same inner diameter. The inner diameters of the internal spaces 63A and 63B are set considering the outer diameter of the four signal wires 25 to be inserted into and passed through the same in a state of being bundled and the thickness required for the shaft body portion 61.

Figure 7:
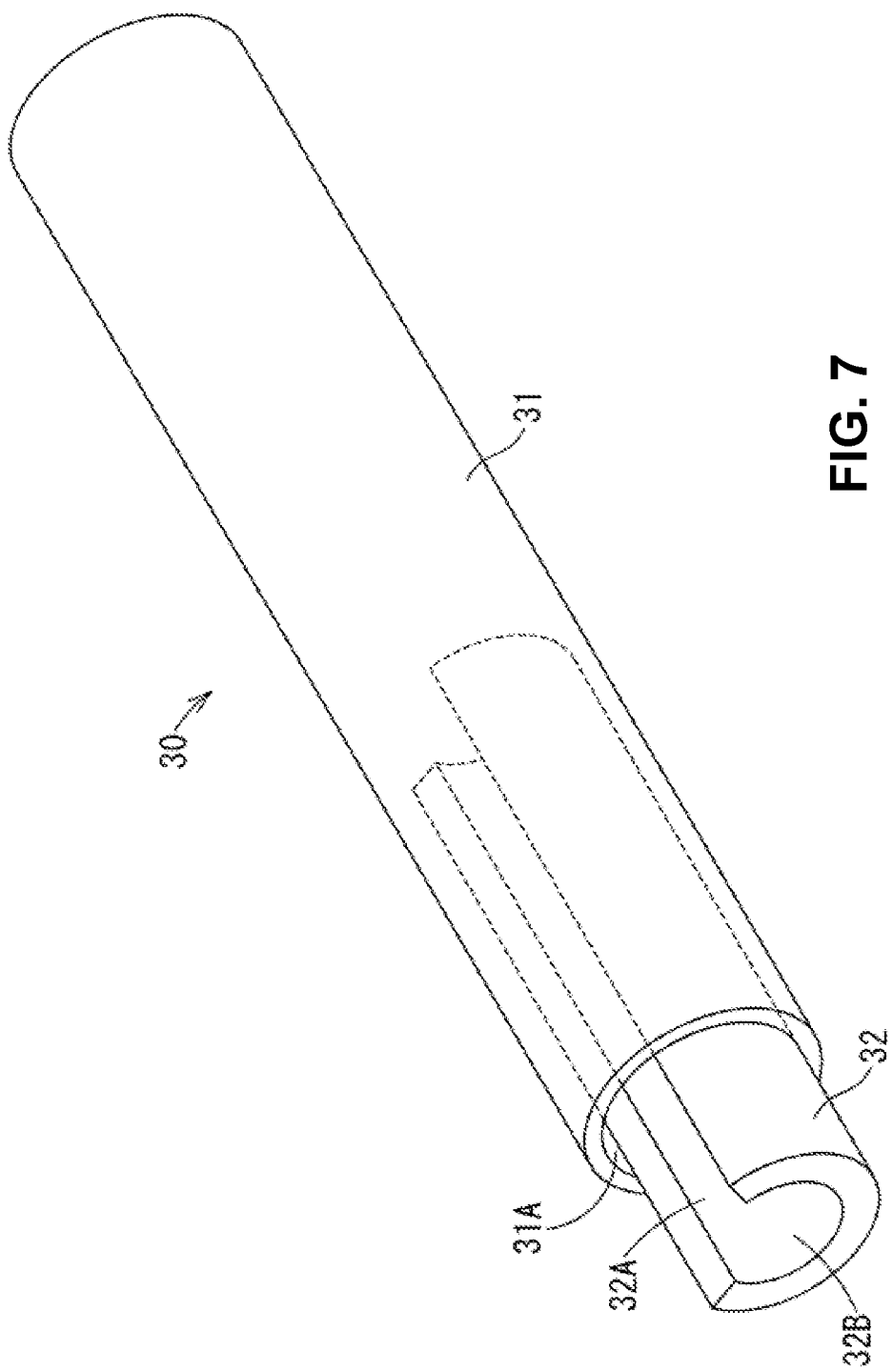
FIG. 7 is a perspective view of a connection member 30.

As illustrated in FIG. 7, a connection member 30 (an example of the connection portion) has a connection body portion 31 and a support portion 32 of a substantially cylindrical shape. In this embodiment, the connection body portion 31 and the support portion 32 each are configured as independent individual members. Due to the fact that the support portion 32 is inserted into the distal end of the connection body portion 31 to be bonded to the connection body portion 31, whereby the connection body portion 31 and the support portion 32 are integrated.

The connection body portion 31 is a tubular body having a constant outer diameter and a constant inner diameter over the axial direction. The connection body portion 31 is formed of stainless steel or resin, such as polyimide, for example. The outer diameter of the connection body portion 31 is equal to the outer diameter of the shaft body portion 61 in the shaft 60. The inner diameter of the connection body portion 31 is equal to the outer diameter of the boss portion 62 in the shaft 60. The proximal end in the connection body portion 31 is fitted into the boss portion 62 of the shaft 60 to be coaxially connected to the shaft 60. The outer diameter of the connection body portion 31 is equal to the outer diameter of the first coil body 21.

The support portion 32 has a C-shaped cross sectional shape. Due to the fact that an opening portion of the C-shaped cross sectional shape continues in the axial direction, a slit 32A extending along the axial direction over the proximal end and the distal end of the support portion 32 is formed. The support portion 32 is formed of stainless steel, for example.

The slit 32A of the support portion 32 occupies an about ⅓ range with respect to the outer periphery of the support portion 32. An internal space 32B of the support portion 32 has an outer diameter equal to the outer diameter around the proximal end of the core material 26 described later. The outer diameter of the support portion 32 is equal to the inner diameter of the connection body portion 31. The length along the axial direction of the support portion 32 is almost half the length along the axial direction of the connection body portion 31.

As illustrated in FIG. 6, the vicinity of the distal end of the support portion 32 is projected from the distal end of the connection body portion 31. The proximal end of the support portion 32 is positioned in an internal space 31A of the connection body portion 31 and does not reach the proximal end of the connection body portion 31. In other words, the proximal end of the support portion 32 is positioned on the side of the distal end relative to the proximal end in the connection body portion 31. Therefore, there is space where the support portion 32 is not present near the proximal end of the internal space 31A of the connection body portion 31.

The core material 26 is inserted into the internal space 32B of the support portion 32. The proximal end of the core material 26 is substantially the same position as the proximal end of the support portion 32. The outer diameter around the proximal end of the core material 26 is equal to the inner diameter of the internal space 32B of the support portion 32. The vicinity of the proximal end of the core material 26 is integrated with the support portion 32 by being inserted into and passed through the internal space 32B of the support portion 32 to be bonded. The outer diameter around the proximal end of the core material 26 is larger than the diameter of the distal end in the internal space 13B of the boss portion 12 in the shaft 10.

[Method for Assembling Blood Measurement Device 50]

The blood measurement device 50 is assembled by connecting the connection member 30 to the tip guide portion 20 assembled beforehand, and then connecting the connection member 30 to the shaft 60.

Figure 8A:
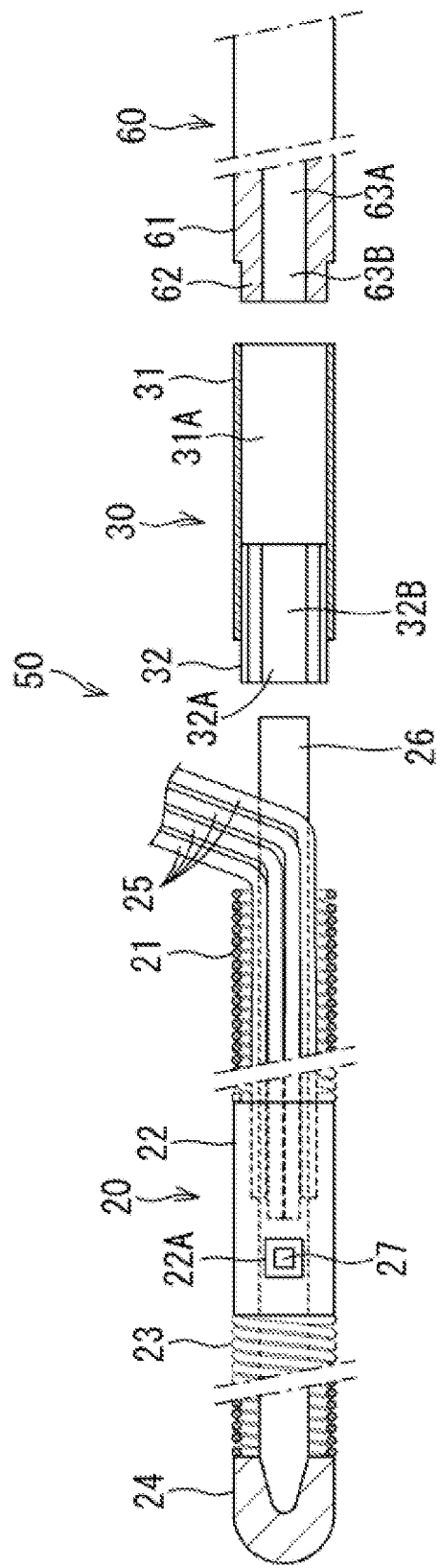
FIG. 8A is an exploded view of the blood measurement device 50 and FIG. 8B is an exploded view of a connection member 30 and a tip guide portion 20 and a shaft 10, which are connected to each other.

The tip guide portion 20 is obtained by integrally assembling the first coil body 21, the element holding body 22, the second coil body 23, the tip member 24, and the core material 26 as illustrated in FIG. 8A. When the tip guide portion 20 has the other constituent members, the other constituent members are also integrally assembled. In the assembled tip guide portion 20, the core material 26 is extended to the outside from the proximal end of the first coil body 21. The four signal wires 25 are also extended to the outside from the proximal end of the first coil body 21.

When the tip guide portion 20 and the connection member 30 are combined, the four signal wires 25 extending from the tip guide portion 20 are brought into a state of being inserted into and passed through the inside of the slit 32A of the support portion 32 and the internal space 31A of the connection body portion 31 to extend to the outside from the proximal end of the connection body portion 31. Then, the core material 26 extending from the tip guide portion 20 is inserted into the internal space 32B of the support portion 32 of the connection member 30. The core material 26 and the support portion 32 are bonded with an adhesive or the like.

The proximal end of the first coil body 21 is fitted onto the outside of the distal end of the support portion 32. The first coil body 21, and the support portion 32 and the connection body portion 31 are bonded with an adhesive.

Figure 8B:
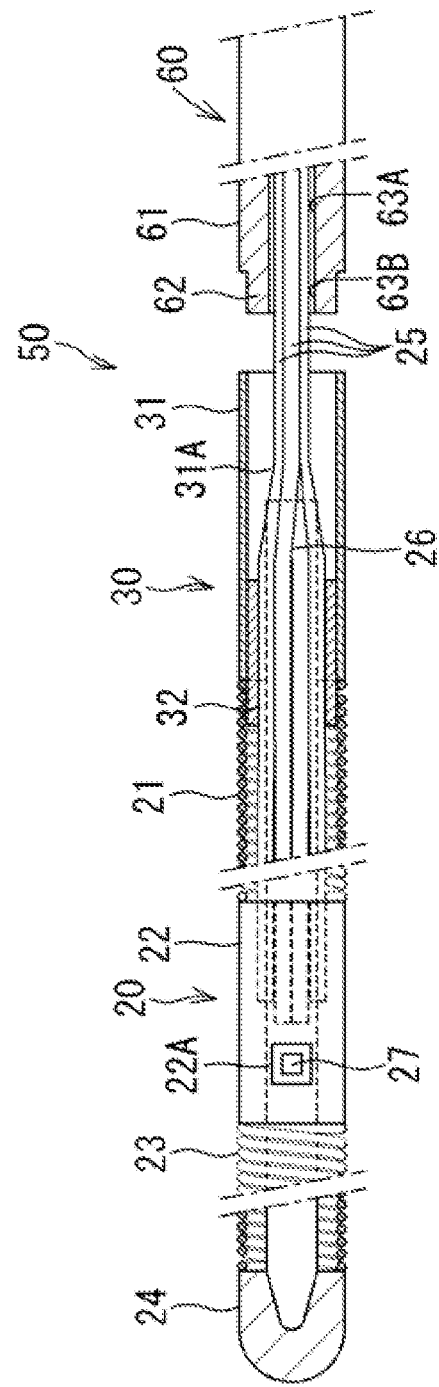

As illustrated in FIG. 8B, the four signal wires 25 extending from the connection body portion 31 of the connection member 30 are inserted into and passed through the internal space 63A of the shaft body portion 61 and the internal space 63B of the boss portion 62 in the shaft 60 to be extended to the outside from the proximal end in the shaft 60. Then, the proximal end of the connection body portion 31 is fitted to the outside of the boss portion 62 in the shaft 60. The connection body portion 31 and the boss portion 62 are bonded with an adhesive. Thus, the blood measurement device 50 is assembled.

[Operational Effects of Second Embodiment]

The same operational effects as those of the first embodiment are demonstrated also by the second embodiment described above.

Since the connection body portion 31 is fitted onto the support portion 32 of the connection member 30, the support portion 32 and the core material 26 are difficult to be broken or the like, even when the connection place between the support portion 32 and the core material 26 is bent.

Since the support portion 32 is positioned on the side of the distal end of the connection body portion 31 in the connection member 30, the space in which the signal wires 25 is movable is formed on the side of the proximal end of the connection member 30. Thus, even when the connection member 30 is bent, the proximal end of the core material 26 and the signal wires 25 become difficult to contact each other.

The proximal end of the core material 26 may be positioned on the distal side relative to the proximal end of the connection body portion 31 in the connection member 30. Therefore, not only the configuration in which the proximal end of the core material 26 is positioned in the internal space 31A of the connection body portion 31 but a configuration in which the proximal end of the core material 26 is positioned in the internal space 32B of the support portion 32 may be acceptable.

The connection member 30 may be configured so that the connection body portion 31 and the support portion 32 are individually configured and may not be configured so that the support portion 32 is inserted into the connection body portion 31. More specifically, a configuration in which the connection body portion 31 and the support portion 32 are integrally molded may be acceptable.

Modification of First Embodiment and Second Embodiment

In the embodiments described above, the passage according to the present invention is formed by the slit 14 formed in the connection portion 12 or the slit 32A formed in the support portion 32. However, in place of the configuration, a groove extending in the axial direction may be formed in the outer peripheral surface of the proximal end of the core material 26 and the internal space of the groove may be used as a passage which the signal wires 25 are inserted into and passed through, for example. The number of the slit or the groove is not limited to one and two or more of the slits or the grooves may be formed, and the signal wires 25 may be separately inserted into and passed through the slits or the grooves.

The measurement element 27 held by the element holding body 22 is not limited to the pressure sensor and may be one capable of measuring the physical quantities of blood in a blood vessel. The measurement elements 27 may also be a flow velocity sensor measuring the flow velocity of blood in a blood vessel, a flow rate sensor measuring the flow rate of blood in a blood vessel flow, a temperature sensor measuring the temperature of blood, or the like, for example. The number of the signal wires connected to the measurement element 27 is not limited to 4 and may be 2, 3, or 5 or more.

Not only the configuration in which the measurement element 27 electrically measures information on the physical quantities of blood but a configuration in which the measurement element 27 optically measures the same may be acceptable. In this case, an optical fiber is used as the signal wire 25.

The embodiments described above are configured so that the tip guide portion 20 has two coils of the first coil body 21 and the second coil body 23, the measurement element 27 is provided in the element holding body 22, and the tip member 24 is provided at the tip of the second coil body 23. However, the tip guide portion 20 is not limited to the configuration described in the embodiments and the tip guide portion 20 may be configured by one coil body and a tip member provided at the tip of the coil body and configured so that the measurement element 27 is provided in the coil body.

The blood measurement device 50 is not limited to the configuration of being used as the guide wire and the blood measurement device 50 may be configured as a catheter.

Third Embodiment

Figure 9:
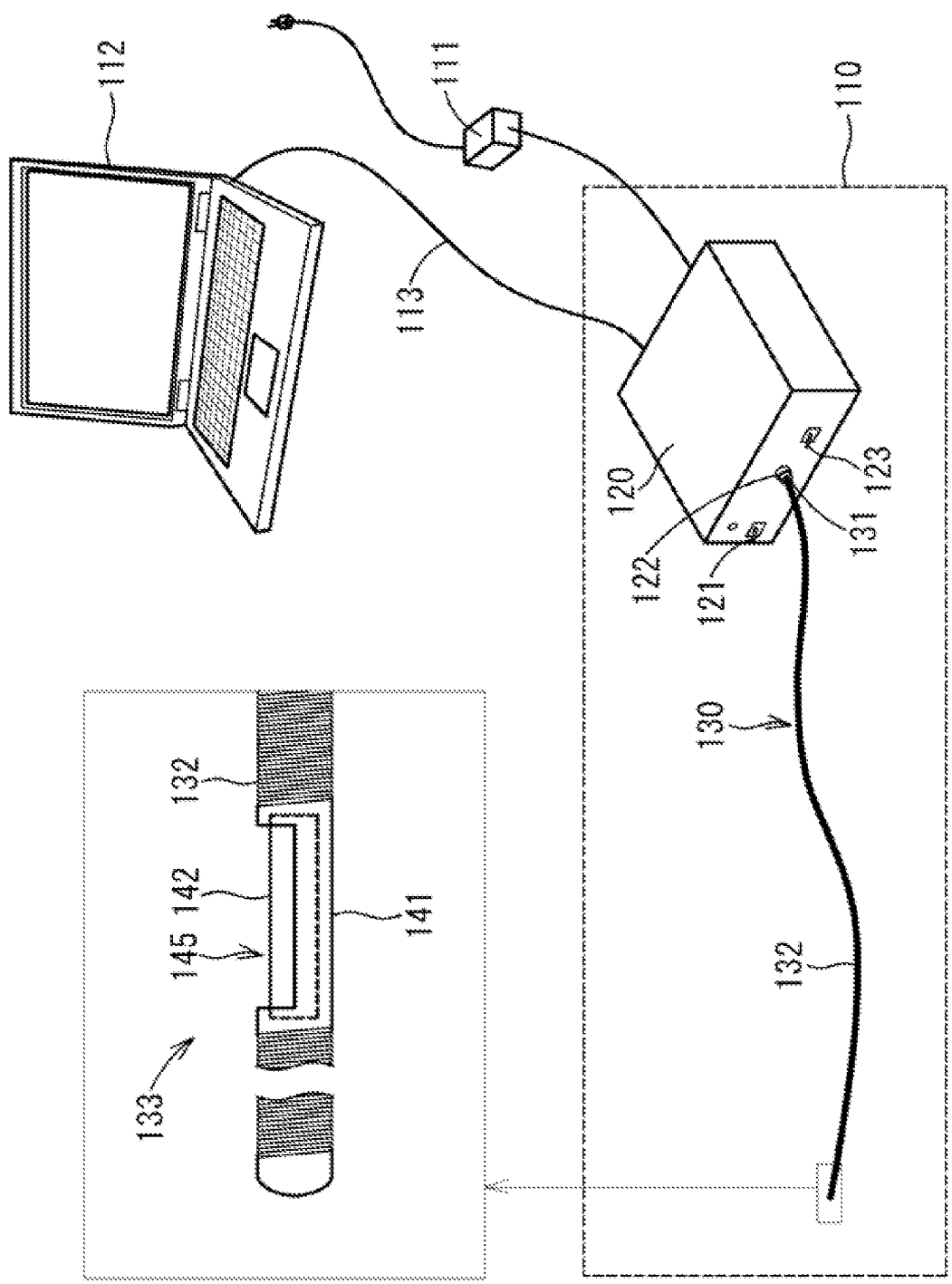
FIG. 9 is an entire configuration diagram illustrating a measurement device 100.

FIG. 9 illustrates a measurement device 100. The measurement device 100 is a device measuring the flow velocity of blood flowing through the inside of a human blood vessel. To the measurement device 100, an AC-DC adapter 111 is connected and a personal computer 112 is connected through a cable 113. The flow velocity of blood is an example of the physical quantity of blood.

The AC-DC adapter 111 is a converter converting a commercial alternating voltage (for example, AC 100 V) into a DC voltage (for example, DC 15 V), and then outputting the converted voltage. The AC-DC adapter 111 may be incorporated in the measurement device 100 to be a part of the measurement device 100.

In the personal computer 112, analysis software is installed. The analysis software analyzes signals input into the personal computer 112 from the measurement device 100, and then displays the analysis results on a monitor.

The measurement device 100 has a body 120 to which the AC-DC adapter 111 and the personal computer 112 are connected and a guide wire 130 connected to the body 120. The guide wire 130 is equivalent to the long member.

The body 120 has a power supply switch 121 turning on/off a power supply input from the AC-DC adapter 111, a sensor connector 122 to which the guide wire 130 is connected, and a function switch 123 on the front surface side. The body 120 has external output connectors 115 (FIG. 12) for connection with the cable 113 and a power supply connector 114 (FIG. 12) to which the AC-DC adapter 111 is connected on the rear surface side. The body 120 has a control circuit 150 (FIG. 12) in a chassis. The control circuit 150 is described later.

The guide wire 130 has a connection connector 131 to be connected to the sensor connector 122 of the body 120, a shaft 132 extending from the connection connector 131, and a sensor 133 disposed at the tip of the shaft 132. The guide wire 130 is attached to the body 120 for each measurement (operation), for example. The "tip" means the end opposite to the end (proximal end) in which the connection connector 131 is provided The shaft 132 has a thickness which allows the insertion of the shaft 132 into a human blood vessel and a length which allows the tip to reach a measurement portion, such as the chest, from an insertion portion, such as the limbs. The shaft 132 is formed by spirally wining stainless steel, for example, and can be bent corresponding to the curve of a blood vessel.

Figure 10:
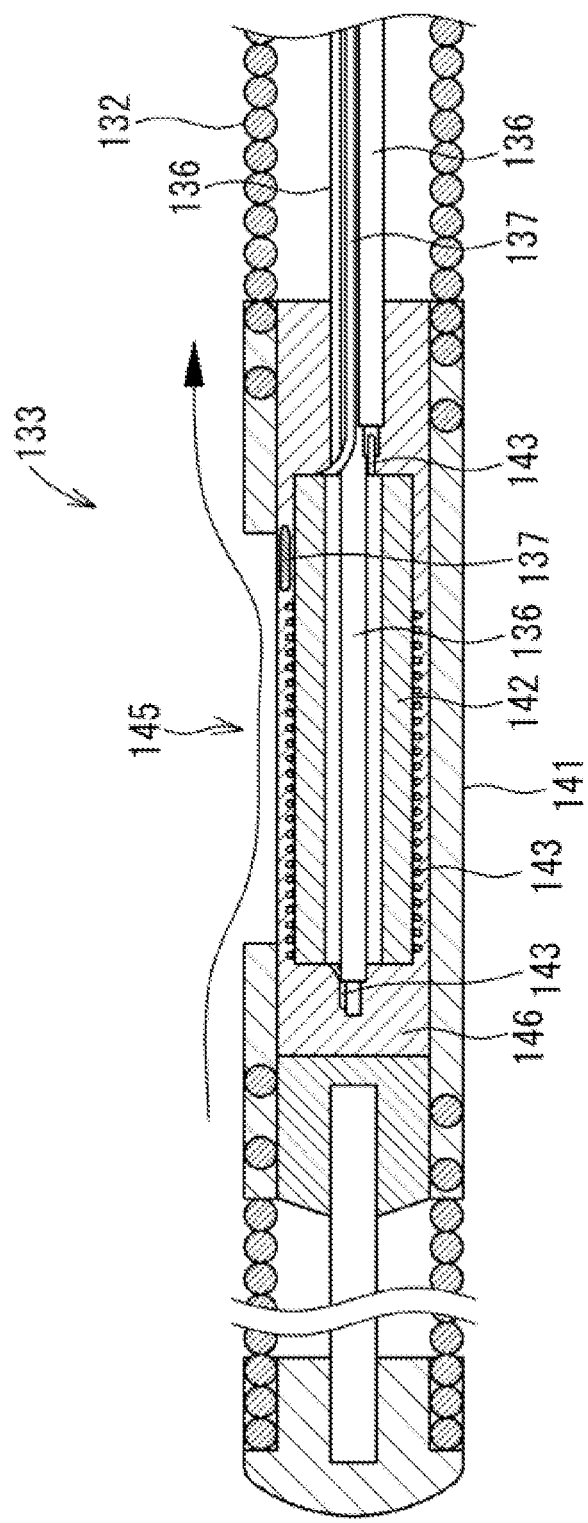
FIG. 10 is a cross-sectional view of a guide wire 130.

As illustrated in FIG. 10, the shaft 132 has a cylindrical shape and is hollow. In the hollow shaft 132, a linear core wire 135 (FIG. 11), a plurality of leads 136, and a thermocouple 137 are disposed. The thermocouple 137 is equivalent to the detection body.

One end (proximal end) of each of the leads 136 and the thermocouple 137 is connected to a terminal of the connection connector 131 (FIG. 9). The leads 136 and the thermocouple 137 are electrically connected to the control circuit 150 (FIG. 12) through the connection connector 131 and the sensor connector 122. The other end (tip) of each of the leads 136 and the thermocouple 137 extends to the tip of the guide wire 130 to be connected to the sensor 133.

Figure 11:
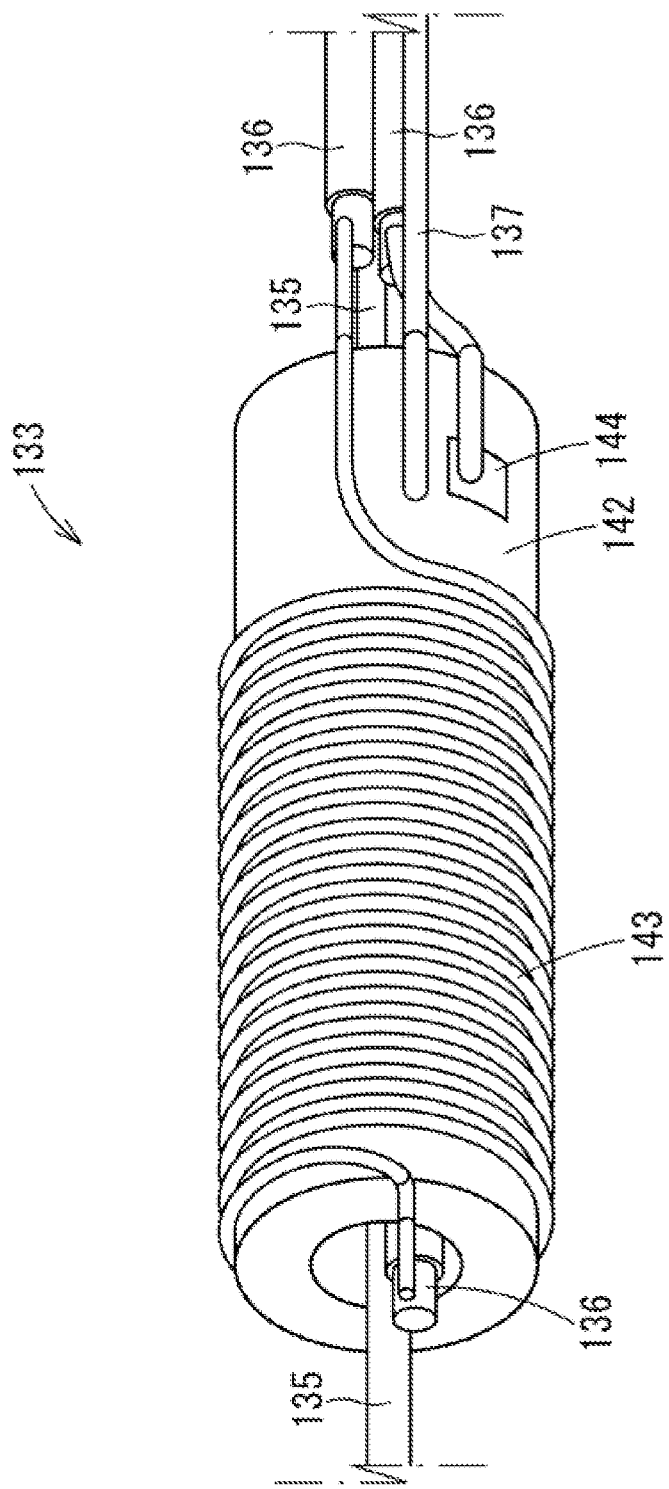
FIG. 11 is a perspective view of a sensor 133.

The sensor 133 has a holder 141, a bobbin 142 held by the holder 141, a heater 143 wound around the bobbin 142, and a detection electrode 144 for leakage current detection (FIG. 11).

The holder 141 has a cylindrical shape having the substantially same diameter as that of the shaft 132. The holder 141 is disposed at the tip of the shaft 132 in such a manner that the axis line is aligned with the axis line of the shaft 132. The holder 141 is fixed to the shaft 132 with an adhesive or the like.

The holder 141 has an opening 145 in the peripheral wall. The opening 145 is provided along the axial direction (horizontal direction in FIG. 10) of the holder 141. The heater 143 is cooled by the blood flow through the opening 145, and then the flow velocity is measured. A detailed description is given later.

The bobbin 142 around which the heater 143 is wound is disposed in the holder 141. The bobbin 142 has a cylindrical shape and is disposed in the holder 141 in such a manner that the axis line is aligned with the axis line of the holder 141.

As illustrated in FIG. 11, the heater 143 is spirally wound around the outer peripheral surface of the bobbin 142. The heater 143 is a resistance wire, such as a nickel wire or a platinum wire, for example. One end (right end in FIG. 11) of the heater 143 is connected to the tip of one lead 136. The other end (left end in FIG. 11) of the heater 143 is connected to the tip of the other one lead 136. The other one lead 136 is drawn out to the left end of the bobbin 142 through the inside of the bobbin 142 to be connected to the other end of the heater 143. The heater 143 receives a DC current supplied by the two leads 136 to generate heat.

The detection electrode 144 is an electrode for detecting a leakage current from the sensor 133 into blood. The detection electrode 144 is disposed on the outer peripheral surface of the bobbin 142 at a position facing the opening 145. For the detection electrode 144, a metal piece fixed to the bobbin 142 or metallic foil vapor-deposited, for example, to the bobbin 142 is usable. The detection electrode 144 is connected to the tip of the lead 136 different from the lead 136 connected to the heater 143. Temporarily, when a leakage current is generated in blood, the leakage current is detected by the detection electrode 144. A detailed description is given later.

The tip of the thermocouple 137 is attached to the outer peripheral surface of the bobbin 142 together with the detection electrode 144. The tip of the thermocouple 137 is disposed at a position facing the opening 145. Therefore, the thermocouple 137 can output a voltage corresponding to the temperature of blood. The output voltage is used for the correction of the flow velocity.

As illustrated in FIG. 10, the holder 141 is filled with a sealing member 146 for insulation between the heater 143 and blood and between the thermocouple 137 and blood or for fixation of the heater 143 and the bobbin 142. The sealing member 146 contains an insulation material. For materials of the sealing member 146, silicon, epoxy, polyamide, polyimide, high-density polyethylene, and the like are used, for example. A configuration in which the detection electrode 144 is not covered with the sealing member 146 is adopted so that a leakage current can be detected. For example, an opening or a notch exposing the detection electrode 144 is provided in the sealing member 146.

A description is given for the measurement of the flow velocity by the sensor 133. A constant DC current (constant current) is supplied to the heater 143 from the body 120 through the two leads 136. Thus, the heater 143 generates heat. The temperature of the heater 143 increases by the generation of heat. The value of resistance of the heater 143 changes by the temperature increase. More specifically, the value of resistance of the heater 143 changes by the supply of the DC current. The change of the value of resistance is dependent on the current value of the DC current to be supplied.

The heater 143 is cooled by the blood flow as described above. When cooled, the value of resistance of the heater 143 changes corresponding to the cooling degree. The cooling degree is dependent on the flow velocity of the blood flow. More specifically, the value of resistance of the heater 143 is dependent also on the flow velocity of blood.

Thus, the change of the value of resistance of the heater 143 is dependent on the current value of the DC current to be supplied and the flow velocity of blood. The current value of the DC current to be supplied is known (preset value). Therefore, when the current value corresponding to the preset value is reduced from the voltage of the heater 143, the voltage corresponding to the flow velocity of the blood flow can be obtained. The flow velocity can be calculated from the voltage. Thus, the sensor 133 is a hot wire flow velocity meter measuring the flow velocity of blood.

Figure 12:
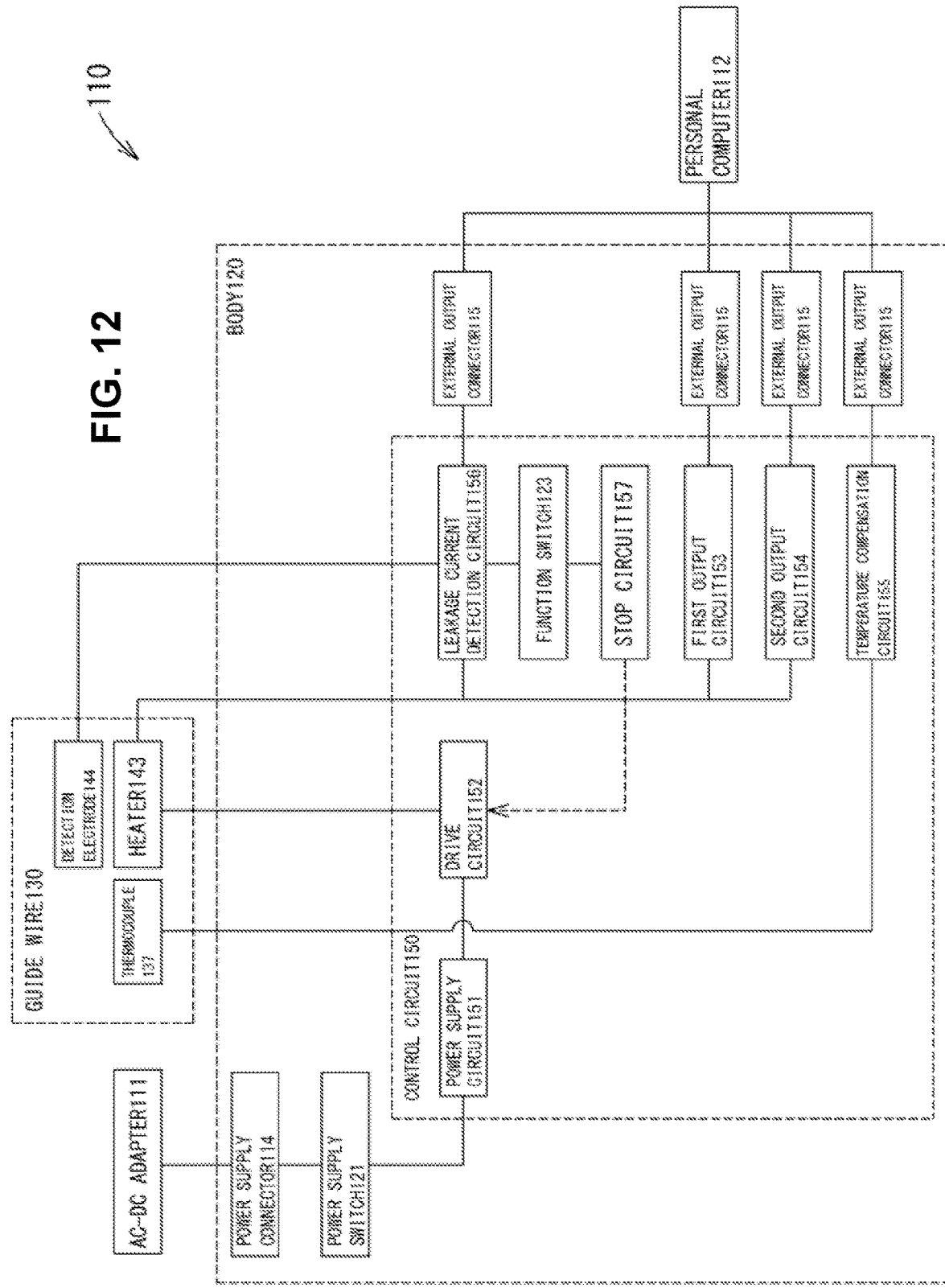
FIG. 12 is a functional block diagram of the measurement device 100.

The supply of the constant current to the heater 143, the detection of the voltage of the heater 143, the detection of the temperature of blood by the thermocouple 137, and the detection of a leakage current are performed by the control circuit 150 illustrated in FIG. 12.

The control circuit 150 is realized by a pattern circuit board, which is not illustrated, disposed in the body 120 and various electronic components, such as an integrated circuit (IC), a resistor, a diode, a capacitor, and a transistor mounted on the circuit board. A single circuit board may be used or a plurality of circuit boards connected to each other by leads may be used.

The control circuit 150 has a power supply circuit 151, a drive circuit 152, a first output circuit 153 outputting a heater voltage, a second output circuit 154 outputting the flow velocity, a temperature compensation circuit 155, a leakage current detection circuit 156, and a stop circuit 157.

The power supply circuit 151 is a DC-DC converter converting a DC voltage of a constant voltage value into a DC voltage of another constant voltage value. The power supply circuit 151 has an input end and one or two or more output ends. The input end is electrically connected to the power supply connector 114 through the power supply switch 121. To the power supply connector 114, the above-described AC-DC adapter 111 is electrically connected. More specifically, a constant DC voltage is input into the power supply circuit 151 from the AC-DC adapter 111. The "electrically connected" described above means conducting by a pattern, a lead wire, and the like of the circuit board.

The power supply circuit 151 converts an input 15 V DC voltage into 5 V, 10 V, 12 V, and the like, for example. The power supply circuit 151 can be configured using one or two or more so-called power supply ICs, such as a switching regulator and a series regulator, for example. Moreover, an insulation type using a transformer may be used for circuit protection or the like. Moreover, a simple constant voltage circuit using a Zener diode and the like may be additionally used.

Figure 13:
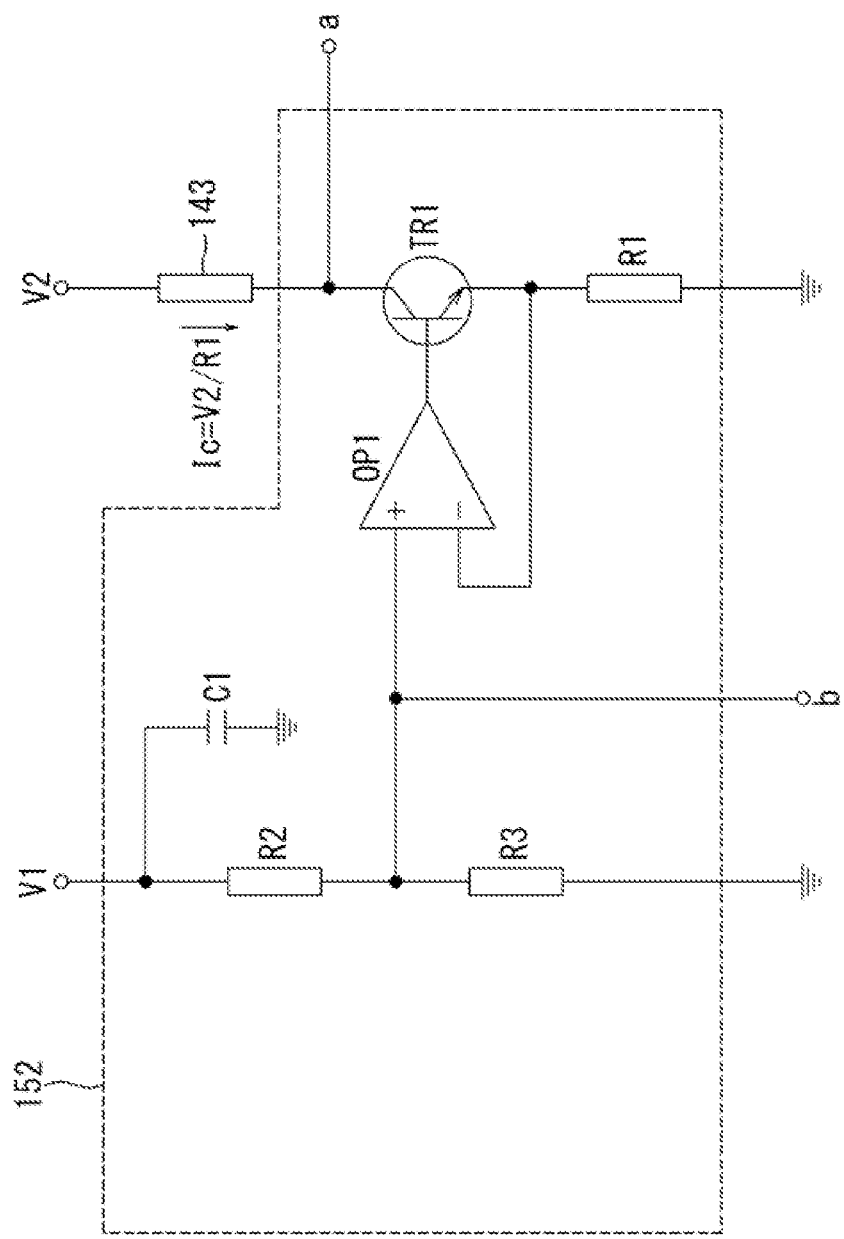
FIG. 13 is a circuit diagram of a drive circuit 152.

One of the output ends of the power supply circuit 151 is connected to the drive circuit 152. The drive circuit 152 is a drive circuit driving the heater 143. Specifically, the drive circuit 152 is configured by a constant current circuit using negative feedback of an operational amplifier as illustrated in FIG. 13 and outputs a constant DC current (constant current).

The drive circuit 152 has two voltage dividing resistors R2 and R3, an operational amplifier OP1, a transistor TR1, a determination resistor R1 determining a current value, and a protection capacitor C1. One end of the protection capacitor C1 is connected to a constant voltage V1 which is one of the output ends of the power supply circuit 151. The other end of the protection capacitor C1 is grounded. The protection capacitor C1 reduces a rush current, for example, when the power supply switch 121 is turned on.

The two voltage dividing resistors R2 and R3 are connected in series, connected to the constant voltage V1 (and the protection capacitor C1) in one end on the side of the voltage dividing resistor R2, and grounded in the other end on the side of the voltage dividing resistor R3. The two voltage dividing resistors R2 and R3 divide the constant voltage V1 and outputs divided voltages from a connection point between the two voltage dividing resistors R2 and R3.

The connection point between the two voltage dividing resistors R2 and R3 are connected to a positive terminal (+) of the operational amplifier OP1. More specifically, the divided voltage is input into the positive terminal (+) of the operational amplifier OP1. The output terminal of the operational amplifier OP1 is connected to a gate of the transistor TR1. On the other hand, a negative terminal (−) of the operational amplifier OP1 is connected to an emitter of the transistor TR1 and is grounded through the determination resistor R1. A collector of the transistor TR1 is connected to a constant voltage V2 which is one of the output ends of the power supply circuit 151 through the heater 143. Therefore, a constant current $Ic=V2/R1$ is supplied to the heater 143. The constant voltages V1 and V2 may be different from each other or may be the same. A variable resistor may be connected in series to the determination resistor R1 for the adjustment of a current value. The constant voltage from the power supply circuit 151 may be directly input into the positive terminal (+) of the operational amplifier OP1 without dividing the constant voltage V1.

Figure 14:
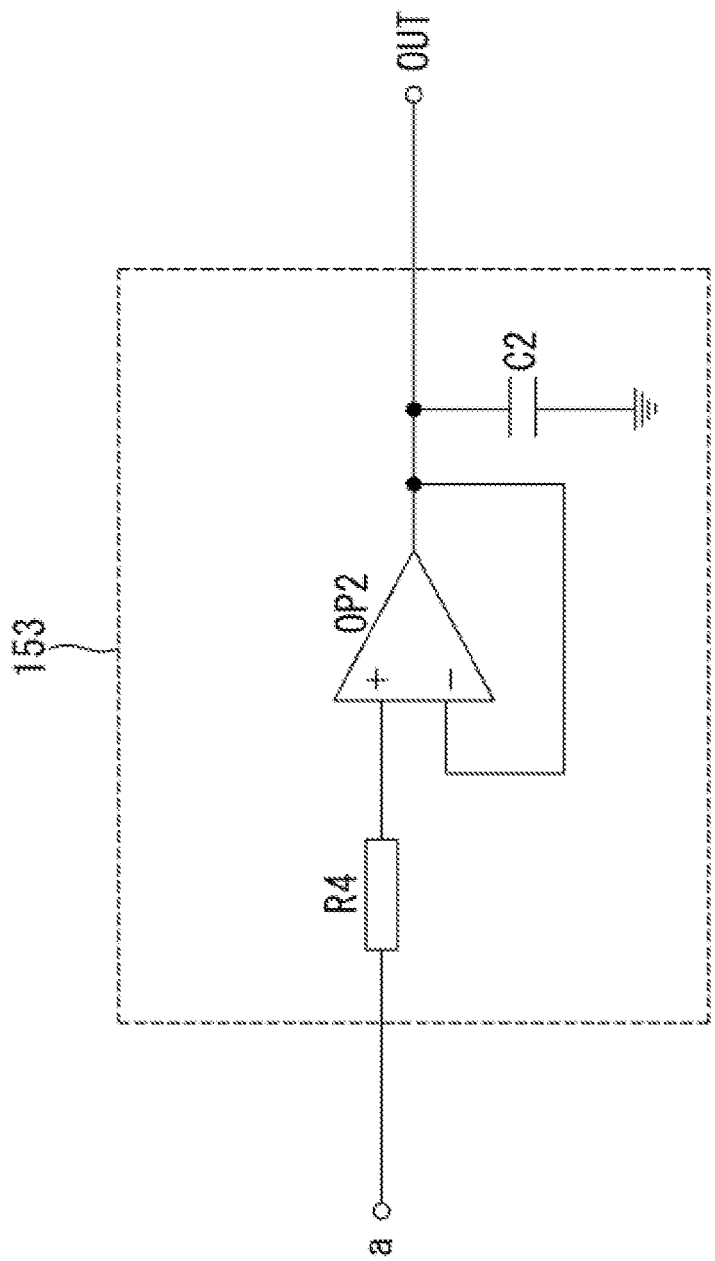
FIG. 14 is a circuit diagram of a first output circuit 153.

The first output circuit 153 illustrated in FIG. 14 is a circuit detecting a voltage (heater voltage) of a collector end (a end of FIG. 13) of the transistor TR1. For the first output circuit 153, a voltage follower using an operational amplifier OP2 is used. Specifically, a positive terminal (+) of the operational amplifier OP2 is connected to the a end through a protection resistor R4 and a negative terminal (−) is connected to the output terminal. Therefore, the operational amplifier OP2 outputs a voltage equal to the voltage of the a end.

The output terminal of the operational amplifier OP2 is electrically connected to one of terminals of the external output connectors 115 (FIG. 12) provided on the rear surface side of the body 120. More specifically, the first output circuit 153 outputs a heater voltage to the outside. The voltage follower is used for the first output circuit 153. This is because impedance conversion for external output is performed. The output terminal of the operational amplifier OP2 is grounded through the capacitor C2 for noise rejection or the like.

Figure 15:
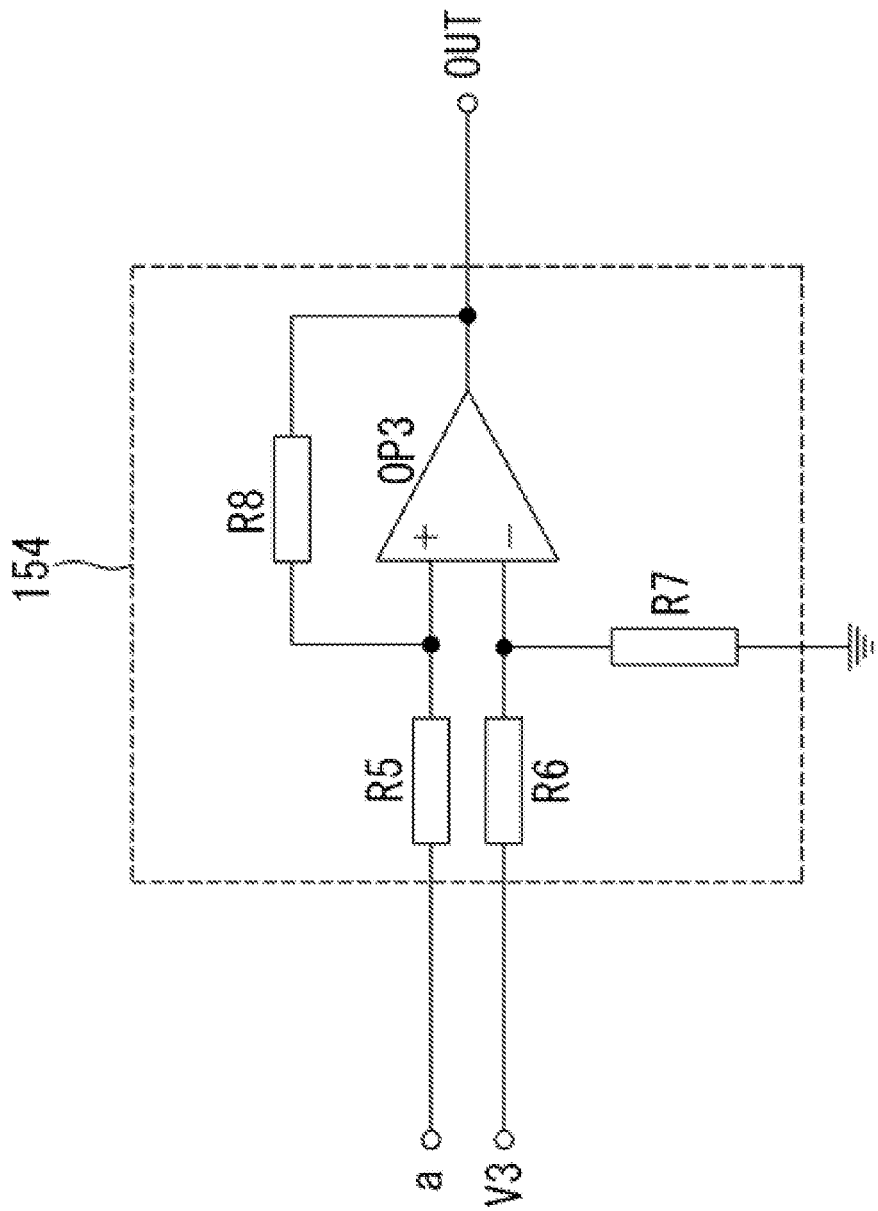
FIG. 15 is a circuit diagram of a second output circuit 154.

The second output circuit 154 illustrated in FIG. 15 is a circuit detecting a change of the heater voltage. For the second output circuit 154, a differential amplifier circuit using an operational amplifier OP3 is used. When specifically described, the second output circuit 154 has the operational amplifier OP3, three protection resistors R5, R6 and R7, and a determination resistor R8.

The positive terminal (+) of the operational amplifier OP3 is connected to the a end through the protection resistor R5. A negative terminal (−) of the operational amplifier OP3 is connected to a constant voltage V3 which is one of the output ends of the power supply circuit 151 through the protection resistor R6 and is grounded through the protection resistor R7. The determination resistor R8 is connected between the positive terminal (+) and the negative terminal (−) of the operational amplifier OP3. The operational amplifier OP3 amplifies a difference between the heater voltage and the constant voltage V3 with an amplification degree corresponding to the determination resistor R8, and then outputs the amplified difference. The constant voltage V3 is set to a voltage equal to the heater voltage when the heater 143 is not cooled by the blood flow, for example. More specifically, when the heater 143 is not cooled by the blood flow, the second output circuit 154 outputs 0 V. However, the constant voltage V3 may be set to another voltage value. For example, the constant voltage V3 may be set to the same voltage as the constant voltage V1 or the constant voltage V2. A voltage obtained by dividing an output voltage from the power supply circuit 151 by the voltage dividing resistor may be set as the constant voltage V3.

The second output circuit 154 configured as described above amplifies and outputs a variation from the reference value (V3) in the heater voltage. The variation is equivalent to the flow velocity. More specifically, the second output circuit 154 outputs a voltage corresponding to the flow velocity of blood. When described in detail, the heater voltage is a value corresponding to a current value of the supplied DC current and the flow velocity of blood as described above. The above-described reference value (V3) is equivalent to the current value of the supplied DC current. Therefore, the above-described variation is equivalent to the flow velocity of blood and the second output circuit 154 outputs a voltage corresponding to the flow velocity of blood.

The output terminal of the operational amplifier OP3 of the second output circuit 154 is electrically connected to one of the external output connectors 115. More specifically, the second output circuit 154 outputs a voltage equivalent to the flow velocity of blood to the outside (personal computer 112).

The temperature compensation circuit 155 is an amplifier circuit which amplifies an output voltage of the thermocouple 137, and then outputs the amplified output voltage to the outside. The temperature compensation circuit 155 converts and amplifies 0° C. to 50° C. to voltages of 0 V to 50 V, and then outputs the converted and amplified voltages. Since a general configuration can be adopted for the temperature compensation circuit 155, a detailed description is omitted. For example, an amplifier circuit using an operational amplifier is usable as the temperature compensation circuit 155. In order to accurately match 0° C. to 0 V and match 50° C. to 50 V, a variable resistor for correction may be provided in the temperature compensation circuit 155. When the temperature compensation of the thermocouple 137 itself is required, a thermocouple compensation circuit may be provided in the temperature compensation circuit 155 or the temperature compensation of the thermocouple 137 itself may be performed from a predetermined formula in the personal computer 112. The (blood) temperature detected by the thermocouple 137 is used for the correction of the flow velocity.

Figure 16:
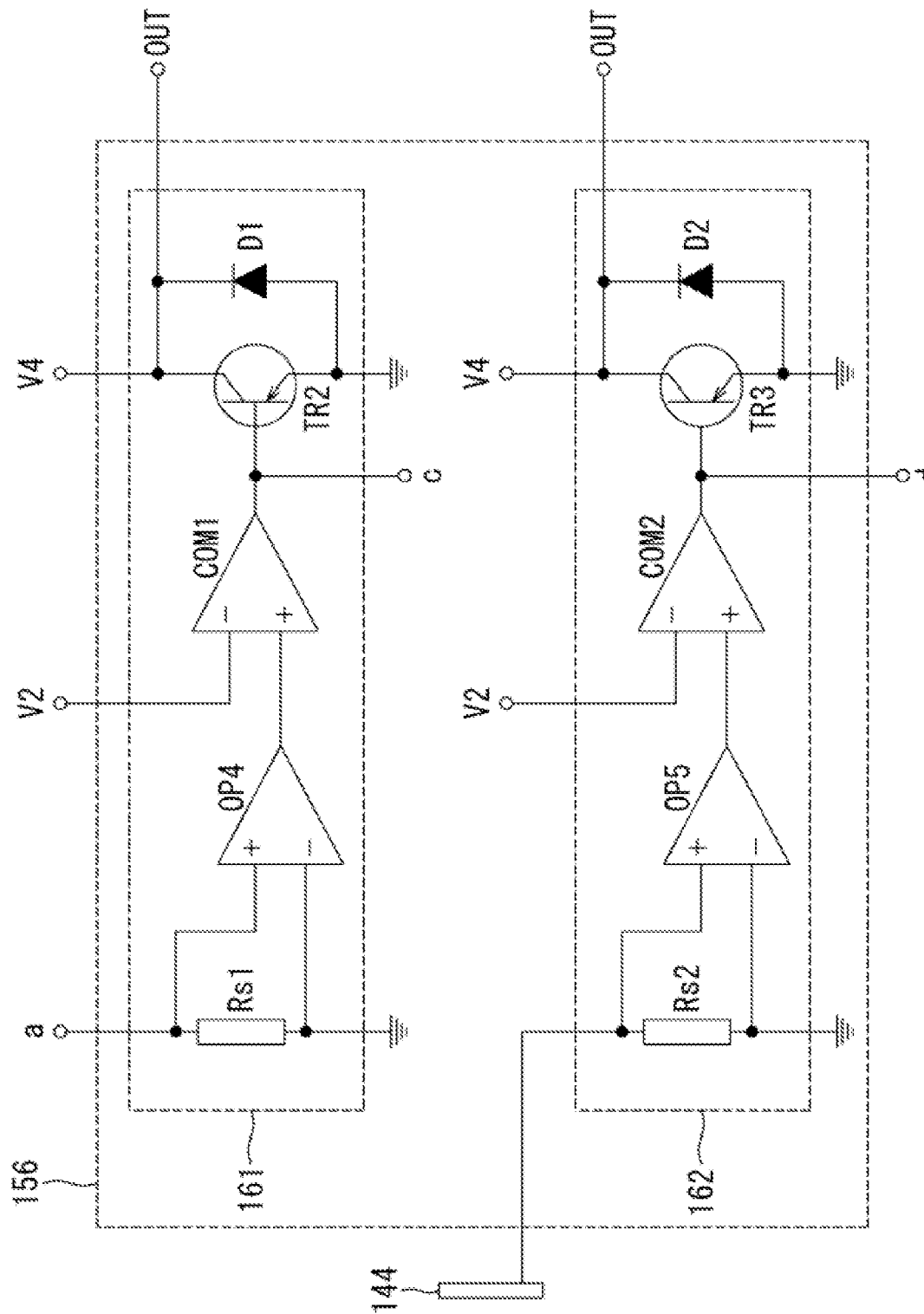
FIG. 16 is a circuit diagram of a leakage current detection circuit 156.

Next, the leakage current detection circuit 156 detecting a leakage current is described. The leakage current detection circuit 156 has a first detection circuit 161 and a second detection circuit 162 as illustrated in FIG. 16. The first detection circuit 161 is a circuit detecting a leakage current from the heater 143 into blood. On the other hand, the second detection circuit 162 is a circuit detecting a leakage current from the entire guide wire 130 into blood.

The first detection circuit 161 has a first shunt resistor Rs1, an operational amplifier OP4 amplifying a voltage between both ends of the first shunt resistor Rs1, and a first comparator COM1 comparing an output of the operational amplifier OP4 with the constant voltage V2. One end (a end) of the first shunt resistor Rs1 is connected to the connection point (a end of FIG. 12) between the heater 143 and the transistor TR1 and the other end is grounded (earthed). Thus, a voltage of a size corresponding to a feedback current from the heater 143 is generated in the first shunt resistor Rs1. The voltage is amplified by the operational amplifier OP4, and then compared with the V2 which is the voltage corresponding to an input current (V2/R1) into the heater 143 in the first comparator COM1. More specifically, the input current and the feedback current are compared in the first comparator COM1. A negative terminal (−) of the first comparator COM1 may be connected to a constant voltage other than the constant voltage V2, and the constant voltage may be set as a comparison target.

Figure 17:
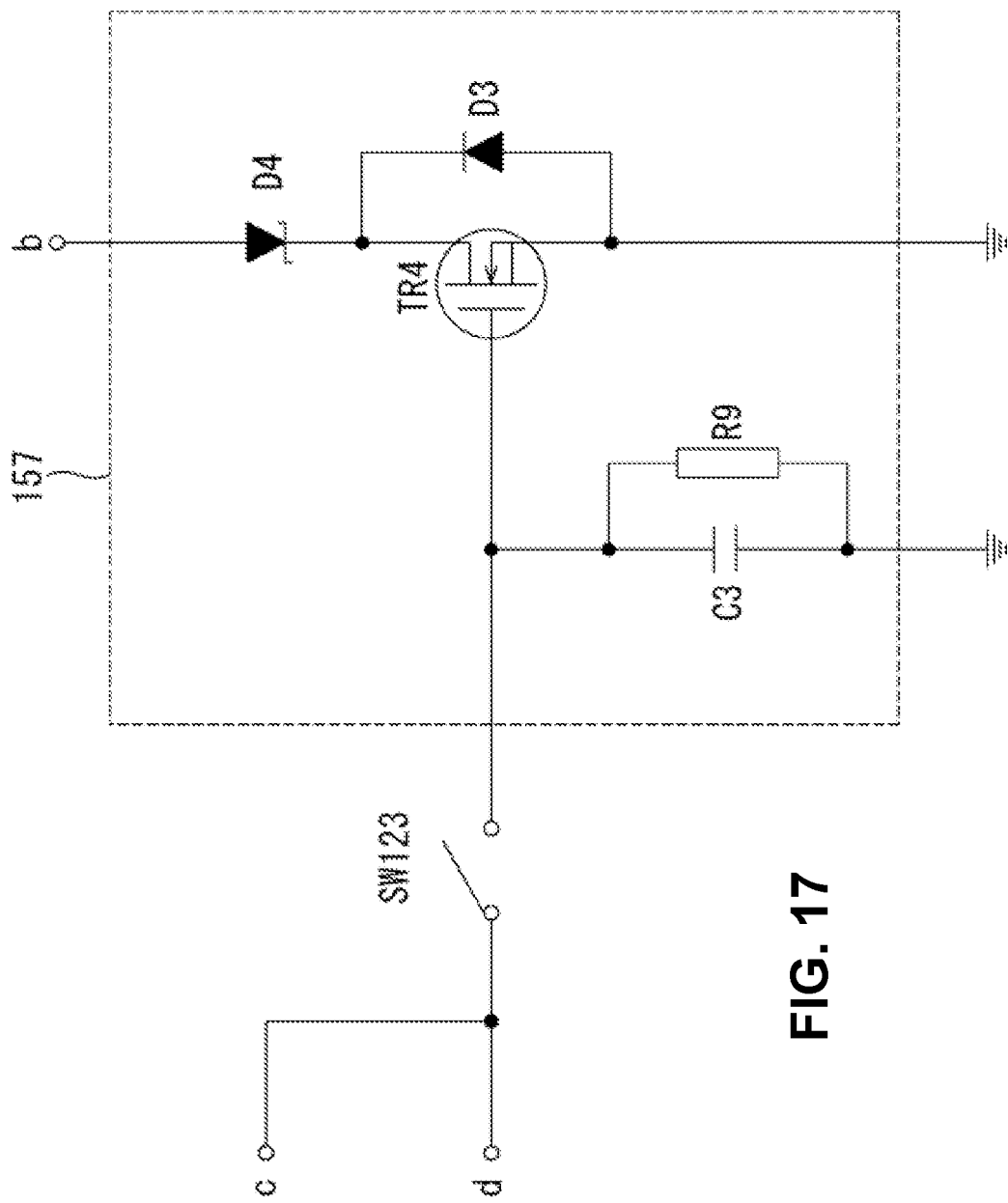
FIG. 17 is a circuit diagram of a stop circuit 157.

The first comparator COM1 outputs 0 V until the leakage current from the heater 143 exceeds a threshold value, and then outputs a constant voltage when the leakage current from the heater 143 exceeds a threshold value. The threshold value is determined by the value of resistance of the first shunt resistor Rs1, the amplification degree of the operational amplifier OP4, and the constant voltage V2. Thus, the first detection circuit 161 judges that the leakage current from the heater 143 into blood exceeding a constant value is a leakage current, and then outputs a constant voltage (first detection signal). The first detection signal is output from a c end of FIG. 16, and then input into the stop circuit 157 described later (FIG. 17).

The first detection signal changes a voltage of an output end (OUT) of the first detection circuit 161. When specifically described, the output terminal of the first comparator COM1 is connected to a base of the transistor TR2 as a switching element. An emitter of the transistor TR2 is grounded. A collector of the transistor TR2 is connected to a constant voltage V4. The collector of the transistor TR2 is electrically connected to one of the external output connectors 115. The transistor TR2 is turned on or off depending on whether the first comparator COM1 outputs the first detection signal. As a result, an output voltage to the external output connector 115 is the constant voltage V4 or 0 V. The constant voltage V4 may be the same voltage as or may be different from V1, V2, and V3. Between the collector and the emitter of the transistor TR2, a diode D1 for prevention of backflow is connected.

The second detection circuit 54 has a second shunt resistor Rs2, an operational amplifier OP5 amplifying and outputting a voltage between both ends of the second shunt resistor Rs2, and a second comparator COM2 comparing an output of the operational amplifier OP5 with the constant voltage V2.

One end of the second shunt resistor Rs2 is connected to the above-described detection electrode 144 and the other end is grounded (earthed). Therefore, a voltage corresponding to a leakage current from the entire guide wire 130 into blood is generated in the second shunt resistor Rs2. The voltage is amplified by the operational amplifier OP5, and then compared with the constant voltage V2 in the second comparator COM2. A negative terminal (−) of the second comparator COM2 may be connected to a constant voltage other than the constant voltage V2, and the constant voltage may be set as a comparison target.

The second comparator COM2 outputs 0 V until the leakage current exceeds a threshold value, and then outputs a constant voltage when the leakage current exceeds a threshold value. The threshold value is determined by the value of resistance of the second shunt resistor Rs2, the amplification degree of an operational amplifier OP6, and the constant voltage V2. Thus, the second detection circuit 162 judges that the leakage current from the entire guide wire 130 into blood exceeding a constant value is a leakage current, and then outputs a constant voltage (second detection signal). The second detection signal is output from a d end of FIG. 16, and then input into the stop circuit 157 described below (FIG. 17).

The second detection signal changes a voltage of an output end (OUT) of the second detection circuit 162. When specifically described, the output terminal of the second comparator COM2 is connected to a base of a transistor TR3 as a switching element. An emitter of the transistor TR3 is grounded. A collector of the transistor TR3 is connected to the constant voltage V4. The collector of the transistor TR3 is electrically connected to one of the external output connectors 115. The transistor TR3 is turned on or off depending on whether the second comparator COM2 outputs the above-described second detection signal. As a result, an output voltage to the external output connector 115 is the constant voltage V4 or 0 V. The constant voltage V4 may be the same voltage as or may be different from V1, V2, and V3. Between the collector and the emitter of the transistor TR2, a diode D2 for prevention of backflow is connected.

The above-described detection signals (first detection signal and second detection signal) output by the leakage current detection circuit 156 are input into the stop circuit 157 illustrated in FIG. 17 through the function switch 123. The stop circuit 157 stops the drive of the drive circuit 152 when a detection signal is input. When described in detail, the stop circuit 157 has a transistor TR4 which is a switching element, a signal maintaining capacitor C3, and a discharge resistor R9. A gate of the transistor TR4 is connected to the c end of the first detection circuit 161 and the d end of the second detection circuit 162 through the function switch 123. The transistor TR4 is turned on by a detection signal output by the first detection circuit 161 or the second detection circuit 162. More specifically, the transistor TR4 is turned on when either the first detection circuit 161 or the second detection circuit 162 detects a leakage current when the function switch 123 is turned on.

A collector (b end) of the transistor TR4 is connected to a b end (FIG. 13) of the drive circuit 152. On the other hand, an emitter of the transistor TR4 is grounded. Therefore, when the leakage current detection circuit 156 detects a leakage current, so that the transistor TR4 is turned on, the positive terminal (+) of the operational amplifier OP1 of the drive circuit 152 is grounded. More specifically, the current supply to the heater 143 is stopped.

One end of the signal maintaining capacitor C3 is connected to the gate of the transistor TR4 and the other end is grounded. Therefore, when the leakage current detection circuit 156 detects a leakage current, the signal maintaining capacitor C3 is charged by a detection signal. On the other hand, the discharge resistor R9 is connected in parallel to the signal maintaining capacitor C3. Charges stored in the signal maintaining capacitor C3 are discharged through the discharge resistor R9.

When charged by the detection signal from the leakage current detection circuit 156, the signal maintaining capacitor C3 maintains the ON operation of the transistor TR3 during a certain period of time, even after the leakage current detection circuit 156 has stopped outputting a detection signal. More specifically, even after the detection signal is stopped, the stop of the current supply to the heater 143 is maintained during a certain period of time. The certain period of time is determined based on the capacity of the signal maintaining capacitor C3 and the value of resistance of the discharge resistor R9. To the stop circuit 157, circuit protection diodes D3 and D4 are connected.

Next, the use of the measurement device 100 is described with reference to FIG. 9 and FIG. 12. First, the guide wire 130 is inserted into a human blood vessel. When the tip of the guide wire 130 reaches a measurement portion (for example, coronary artery), the power supply switch 121 and the function switch 123 of the body 120 are turned on, so that the sensor 133 is driven. More specifically, a constant current is supplied to the heater 143 from the drive circuit 152. In that case, the first output circuit 153 outputs a heater voltage, the second output circuit 154 outputs a voltage corresponding to the flow velocity of blood, and the temperature compensation circuit 155 amplifies and converts an output of the thermocouple 137, and then outputs the amplified and converted output. The leakage current detection circuit 156 monitors the presence or absence of a leakage current. Specifically, the first detection circuit 161 monitors a leakage current from the heater 143 into blood and the second detection circuit 162 monitors a leakage current from the guide wire 130 into blood. Before the guide wire 130 is inserted into a human blood vessel, the power supply switch 121 and the function switch 123 may be turned on.

The heater voltage detected by the first output circuit 153, the voltage (flow velocity voltage) output by the second output circuit 154, and the signal voltage output when the leakage current detection circuit 156 detects a leakage current are output from the external output connectors 115, and then input into the personal computer 112 through the cable 113. In the personal computer 112, the flow velocity is calculated from the flow velocity voltage by installed analysis software. The "calculation" includes the calculation by a formula (stored in the analysis software beforehand) and the determination of the flow velocity using a flow velocity determination table (stored in the analysis software beforehand) indicating the correspondence relationship between the flow velocity voltage and the flow velocity.

The calculated flow velocity is corrected by an input voltage input from the temperature compensation circuit 155. For example, a correction value is calculated by the formula input beforehand or a correction value is determined using the conversion table indicating the correspondence relationship between the input voltage and the correction value. The flow velocity is corrected by the determined correction value.

The corrected flow velocity and the above-described heater voltage are displayed on a monitor. When the leakage current detection circuit 156 detects a leakage current, the supply of the constant current to the heater 143 is stopped, and then a signal voltage transmitting the detection of the leakage current is input into the personal computer 112, so that the detection of the leakage current is displayed on a monitor or an alarm is issued. In the personal computer 112, the pressure of blood may be calculated from the calculated flow velocity, and then the calculated pressure may be displayed on a monitor Operational Effects of Third Embodiment The measurement device 100 according to the third embodiment can detect that a constant leakage current is generated by the leakage current detection circuit 156. The detection of the leakage current can be output to the outside, and then displayed on a monitor or an alarm can be issued.

Since the function switch 123 is provided, a drive stop function of the sensor 133 by the stop circuit 37 can be turned off when it is not appropriate to stop the drive of the sensor 133 or the drive of the sensor 133 needs to resume.

Since the thermocouple 137 and the temperature compensation circuit 155 are provided, the temperature of the calculated flow velocity can be corrected.

Since the detection circuits of both the first detection circuit 161 and the second detection circuit 162 are provided in the leakage current detection circuit 156, both the leakage current from the heater 143 and the leakage current from the entire guide wire 130 can be separately detected.

Since the stop circuit 157 is provided, the current supply to the heater 143 is immediately stopped when a leakage current is detected. Moreover, since the signal maintaining capacitor C3 is provided, the current supply to the heater 143 is prevented from being frequently turned on/off (chattering).

Modification of Third Embodiment

The third embodiment describes the example in which the leakage current detection circuit 156 has the first detection circuit 161 and the second detection circuit 162. However, the leakage current detection circuit 156 may have only the first detection circuit 161 or only the second detection circuit 162.

The third embodiment describes the configuration in which the signal voltage from the first detection circuit 161 and the signal voltage from the second detection circuit 162 are individually input into the personal computer 112. However, only the signal voltage from the first detection circuit 161 or only the signal voltage from the second detection circuit 162 may be input into the personal computer 112. A configuration may be adopted in which, when an output end of the first detection circuit 161 and an output end of the second detection circuit 162 are connected, so that at least either one of the first detection circuit 161 and the second detection circuit 162 detects a leakage current, a signal voltage transmitting the detection of the leakage current is input into the personal computer 112.

The third embodiment describes the configuration in which the flow velocity is corrected and calculated with the personal computer 112. However, the calculation and the correction of the flow velocity may be performed in the control circuit 150. For example, the flow velocity may be corrected and calculated by converting an output of the thermocouple 137 into a suitable voltage using an amplifier circuit, and then inputting the converted voltage and the heater voltage into a differential amplifier circuit. Thus, a voltage equivalent to the corrected and calculated flow velocity is output to the personal computer 112 through the external output connectors 115.

The third embodiment describes the example in which the thermocouple 137 is provided in the guide wire 130. However, a reference heater may be provided in place of the thermocouple 137. For the reference heater, one having the same configuration as that of the heater 143 is used. The reference heater is provided at the tip of the guide wire 130 as with the heater 143. However, the reference heater is provided so as not to be exposed to blood. Therefore, the voltage of the reference heater is a value not dependent on the flow velocity of blood and dependent on the temperature of blood. The voltage of the reference heater is output to the outside from the temperature compensation circuit 155. The personal computer 112 determines a correction value by the voltage of the reference heater, and then corrects the flow velocity. The reference heater is equivalent to the detection body for use in the temperature compensation as with the thermocouple 137. The calculation and the correction of the flow velocity can also be performed not with the personal computer 112 but with the control circuit 150. For example, a differential amplifier circuit which amplifies and outputs a difference between the voltage of the heater 143 and the voltage of the reference heater is provided in the control circuit.

The third embodiment describes the configuration in which the flow velocity is corrected by the thermocouple 137. However, a configuration in which the thermocouple 137 is not provided can also be adopted. For example, supposing that the temperature of blood is a predetermined value, the flow velocity may be corrected by a correction value corresponding to the predetermined value. Alternatively, the body temperature of a patient is measured before an operation, and then the flow velocity may be corrected by a correction value corresponding to the measured body temperature.

The third embodiment describes the example using the constant current circuit using negative feedback of the operational amplifier as the drive circuit 152. However, other constant current circuits may be used.

The third embodiment describes the example in which, when a leakage current is detected, the drive of the sensor 133 is stopped during a certain period of time by the signal maintaining capacitor C3. However, another configuration, e.g., a configuration in which, when a leakage current is detected once, the drive of the sensor 133 is continuously stopped unless manually reset, may be adopted. For example, an electromagnetic relay or the like which can be manually reset may be provided in place of the transistor TR4 in the stop circuit 157.

The third embodiment describes the configuration in which, when a leakage current is detected, the supply of a constant current from the drive circuit 152 to the heater 143 is stopped. However, when a leakage current is detected, the power supply switch 121 itself may be turned off.

The third embodiment describes the configuration in which the flow velocity is calculated or displayed utilizing the personal computer 112. However, a configuration not using the personal computer 112 is also acceptable. For example, a microcomputer replacing the analysis software is provided in the control circuit 150, a liquid crystal display unit replacing the monitor is provided in the body 120, and a display driver IC and the like are further provided in the control circuit 150. When the configuration is adopted, it is not necessary to connect the personal computer 112 to the body 120, and the heater voltage, the flow velocity, the presence or absence of leakage current detection, and the like are displayed on the liquid crystal display unit in the body 120.

It is a matter of course that the control circuit 150 of the present invention is usable for flow velocity meters other than the sensor 133, blood pressure sensors, such as the measurement element 27, and the like.

Other Modifications

The measurement of the pressure and the flow velocity of blood may be always performed or may be intermittently performed. Specifically, the drive circuit 152 may always output a constant current or may intermittently output a constant current. For example, a switching element is provided in an output end of the drive circuit 152, and then a drive signal of a constant frequency is input into the switching element to turn on/off the switching element. As a result, the drive circuit 152 intermittently outputs a constant current. In addition, an intermittent output of a constant current can be performed using existing techniques.

Due to the fact that the measurement of the pressure and the flow velocity of blood is intermittently performed, the measurement accuracy is improved. When specifically described, when a leakage current is generated, the voltage level of a reference voltage may shift. The reference voltage is the ground or a generated constant voltage. When the voltage level shifts, the detection accuracy decreases. Due to the fact that a constant current is intermittently output, the shift of the voltage level of the reference voltage is suppressed. As a result, the measurement accuracy is improved.

It is desirable that, when a constant current is intermittently output, a duty ratio which is a ratio of a period in which a constant current is output to a period in which a constant current is not output is made variable. For a technique of varying the duty ratio, existing techniques are usable. It is desirable that the change of the duty ratio can be performed from the outside with a potentiometer (digital variable resistor) or the like. For example, when the amount of a leakage current is large, the duty ratio is decreased. When the amount of a leakage current is small, the duty ratio is increased.

REFERENCE SIGNS LIST

10, 60 Shaft
11, 61 Shaft body portion
12 Connection portion
14, 32A Slit (Passage)
15 Cover member
20 Tip guide portion
21 First coil body
22 Element holding body
23 Second coil body
24 Tip member
25 Signal wire
26 Core material
27 Measurement element
30 Connection member (Connection portion)
31 Connection body portion
32 Support portion
50 Blood measurement device
110 Measurement device
123 Function switch
132 Shaft (Long member)
133 Sensor
137 Thermocouple (Detection body)
150 Control circuit
152 Drive circuit (Constant current circuit)
155 Temperature compensation circuit
156 Leakage current detection circuit
157 Stop circuit
161 First detection circuit
162 Second detection circuit
Rs1 First shunt resistor
Rs2 Second shunt resistor
COM1 First comparator
COM2 Second comparator
C3 Signal maintaining capacitor
R9 Discharge resistor

The invention claimed is:

1. A control circuit for a sensor provided in an elongated member insertable into a lumen to measure a physical quantity of a fluid in the lumen, the control circuit comprising:
a drive circuit configured for supplying a drive current to the sensor,
a leakage current detection circuit, and
a stop circuit;
wherein the leakage current detection circuit includes:
a shunt resistor configured for converting, into a voltage, one of either a feedback current from the or a leakage current, and
a comparator configured to receive a detection voltage corresponding to the voltage from the shunt resistor and a constant voltage, the comparator configured to output a detection signal in a first state when the detection voltage is larger than the constant voltage;
wherein the stop circuit is configured for stopping supply of the drive current to the in response to the detection signal output from the comparator;
wherein the drive circuit comprises a first operational amplifier and has a drive-circuit first input and a drive-circuit second input coupled to a common input of the first operational amplifier;
wherein the drive-circuit first input is a constant-voltage first signal; and
wherein the stop circuit is configured to provide the drive-circuit second input to the drive circuit, wherein the drive-circuit second input has a ground state when the detection signal is in the first state.

2. The control circuit according to claim 1,
wherein the leakage current detection circuit includes either one or both of a first detection circuit and a second detection circuit, and the leakage current is either one or both of a first leakage current and a second leakage
wherein the shunt resistor configured for converting into the voltage includes either one or both of a first shunt resistor configured for converting into a first voltage and a second shunt resistor configured for converting into a second voltage;

wherein the comparator configured to receive the detection voltage and output the detection signal includes either one or both of a first comparator configured to receive a first detection voltage and output a first detection signal, and a second comparator configured to receive a second detection voltage and output a second detection signal;

wherein the first detection circuit comprises the first shunt resistor and the first comparator, and the second detection circuit comprises the second shunt resistor and the second comparator;

wherein the first shunt resistor configured for converting into the first voltage converts the feedback current into the first voltage, wherein the feedback current corresponds to a difference between a predetermined current and the first leakage current, the predetermined current corresponding to one of either the drive current of the or a constant current, and the first comparator is configured to receive the first detection voltage corresponding to the first voltage from the first shunt resistor and the constant voltage, wherein the second shunt resistor configured for converting into the second voltage converts the second leakage current into the second voltage, wherein the second leakage current flows between the fluid and a ground, and the second comparator is configured to receive the second detection voltage corresponding to the second voltage from the second shunt resistor and the constant voltage, and wherein the stop circuit is configured for stopping supply of the drive current to the sensor in response to at least one of the first detection signal output from the first detection circuit and the second detection signal output from the second detection circuit.

3. The control circuit according to claim 2, wherein the stop circuit includes:

a switching element configured for turning on and off supply of the drive current to the sensor in response to either one or both of the first detection signal and the second detection signal; and a signal maintaining capacitor configured for being charged by either one or both of the first detection signal and the second detection signal and maintaining the switching element in a conduction state.

4. The control circuit according to claim 1, further comprising:

a function switch configured for turning on or off an input of the detection signal from the leakage current detection circuit to the stop circuit.

5. The control circuit according to claim 1, further comprising:

a temperature compensation circuit configured for receiving an input from a detection body provided in the sensor.

6. A measurement device comprising:

the control circuit according to claim 1; and the sensor.

7. The measurement device according to claim 6, wherein the sensor is a hot wire flow velocity meter.

* * * * *